(12) United States Patent
Sterzer et al.

(10) Patent No.: US 8,447,385 B2
(45) Date of Patent: May 21, 2013

(54) HANDHELD MEDICAL MICROWAVE RADIOMETER

(75) Inventors: Fred Sterzer, Princeton, NJ (US); Daniel D. Mawhinney, Livingston, NJ (US); Laleh Rabieirad, Ithaca, NY (US); David E. Quinn, Auburn, NY (US); John A. Lane, Weedsport, NY (US); Matthew D. Mullin, Memphis, NY (US); Charles N. Stewart, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 252 days.

(21) Appl. No.: 12/845,447

(22) Filed: Jul. 28, 2010

(65) Prior Publication Data

US 2012/0029359 A1 Feb. 2, 2012

(51) Int. Cl.
*A61B 5/055* (2006.01)
*A61B 5/00* (2006.01)
*G01J 5/00* (2006.01)

(52) U.S. Cl.
USPC .......................... 600/430; 600/549; 374/122

(58) Field of Classification Search .................. 600/430, 600/549; 374/121, 122, 129; 607/156
See application file for complete search history.

(56) References Cited

U.S. PATENT DOCUMENTS

| | | | |
|---|---|---|---|
| 4,190,053 A | 2/1980 | Sterzer | |
| 4,197,860 A | 4/1980 | Sterzer | |
| 5,149,198 A | 9/1992 | Sterzer | |
| 5,176,146 A | 1/1993 | Chive et al. | |
| 5,341,814 A | 8/1994 | Van De Velde et al. | |
| 5,357,224 A | 10/1994 | Sterzer | |
| 5,688,050 A | 11/1997 | Sterzer et al. | |
| 5,949,845 A | 9/1999 | Sterzer | |
| 2005/0053118 A1 | 3/2005 | Stephan et al. | |
| 2005/0190815 A1 | 9/2005 | Lee et al. | |

OTHER PUBLICATIONS

International Search Report and Written Opinion, PCT/US2011/040455, Feb. 24, 2012.
Land, D. V., An Efficient, Accurate and Robust Radiometer Configuration for Microwave Temperature Measurement for Industrial and Medical Applications, Journal of Microwave Power and Electromagnetic Energy, International Microwave Power Institute, vol. 36, No. 3, pp. 139-153, 2001.
Arunchalam, K. et al., Characterization of a digital microwave radiometry system for noninvasive thermometry using a temperature-controlled homogeneous test load, Physics in Medicine and Biology, Phys. Med. Biol. 53, pp. 3883-3901, Jul. 2008.

(Continued)

*Primary Examiner* — Michael Rozanski

(57) ABSTRACT

A microwave handheld radiometer for measuring subsurface tissue temperature of a subject includes a microwave antenna disposed relative to a handheld radiometer housing and adapted to electromagnetically couple to a skin surface of a subject, a circulator having a first circulator input and a second circulator input, wherein the first circulator input is electrically coupled to said antenna via a microwave feedline. A switch is electrically disposed between the antenna and an microwave feedline, said switch having a calibrate state and a measure state. A noise source, electrically coupled to the circulator, is being configured to provide a first source of thermal noise at a first temperature and a second source of thermal noise at a second temperature, wherein the noise source is switched between the first source and second source upon external command wherein a detector provides an output wherein surface temperature effects are corrected for the sub-surface measurement.

34 Claims, 20 Drawing Sheets

OTHER PUBLICATIONS

Sterzer, F., Microwave Radiometers for Non-Invasive Measurements of Subsurface Tissue Temperatures, Automedica, 1987, vol. 8, pp. 203-211, Gordon and Breach Science Publishers, Inc.

Johnson, C. C., et al., Nonionizing Electromagnetic Wave Effects in Biological Materials and Systems, Proceedings of the IEEE, vol. 60, pp. 692-718, Jun. 1972.

Turner, P. F., et al., Computer Solutions for Applicator Heating Patterns, NCI Third International Symposium: Cancer Therapy, Hyperthermia, Drugs, and Radiation, monograph 61, pp. 521-523, Jun. 1980.

Nikawa Y. et al., Development and Testing of a 2450-MHz Lens Applicator for Localized Microwave Hyperthermia, IEEE Trans. Microwave Theory and Techniques, Nov. 1985.

Brown, G. H., Directional Antennas, Proc. IRE, vol. 25, No. 1, Jan. 1937.

Cheston, T. C., et al., Skolnik, M. I., Editor, Radar Handbook, Second Edition, Chapter 7.2 "Array Theory", McGraw Hill Publishing Company, 1990.

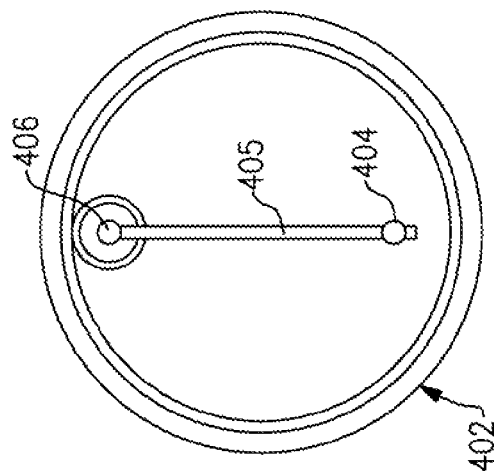
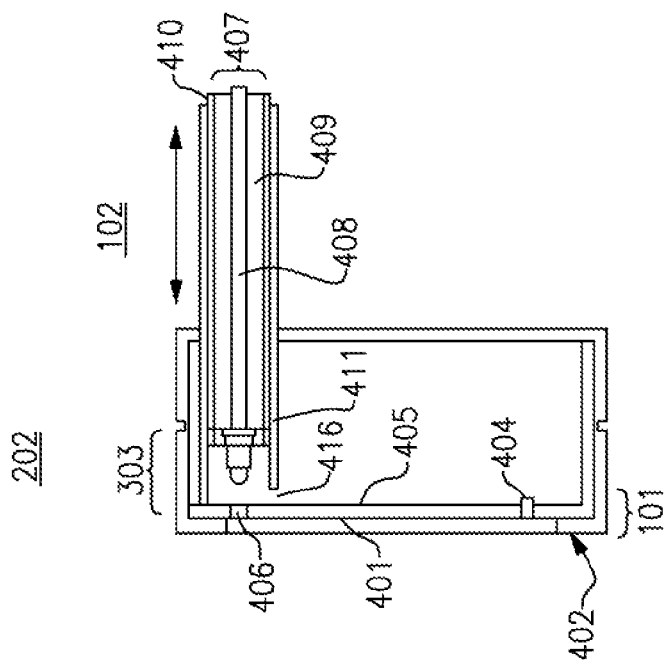
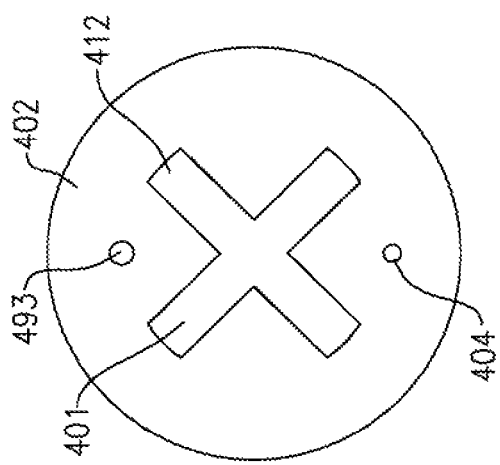

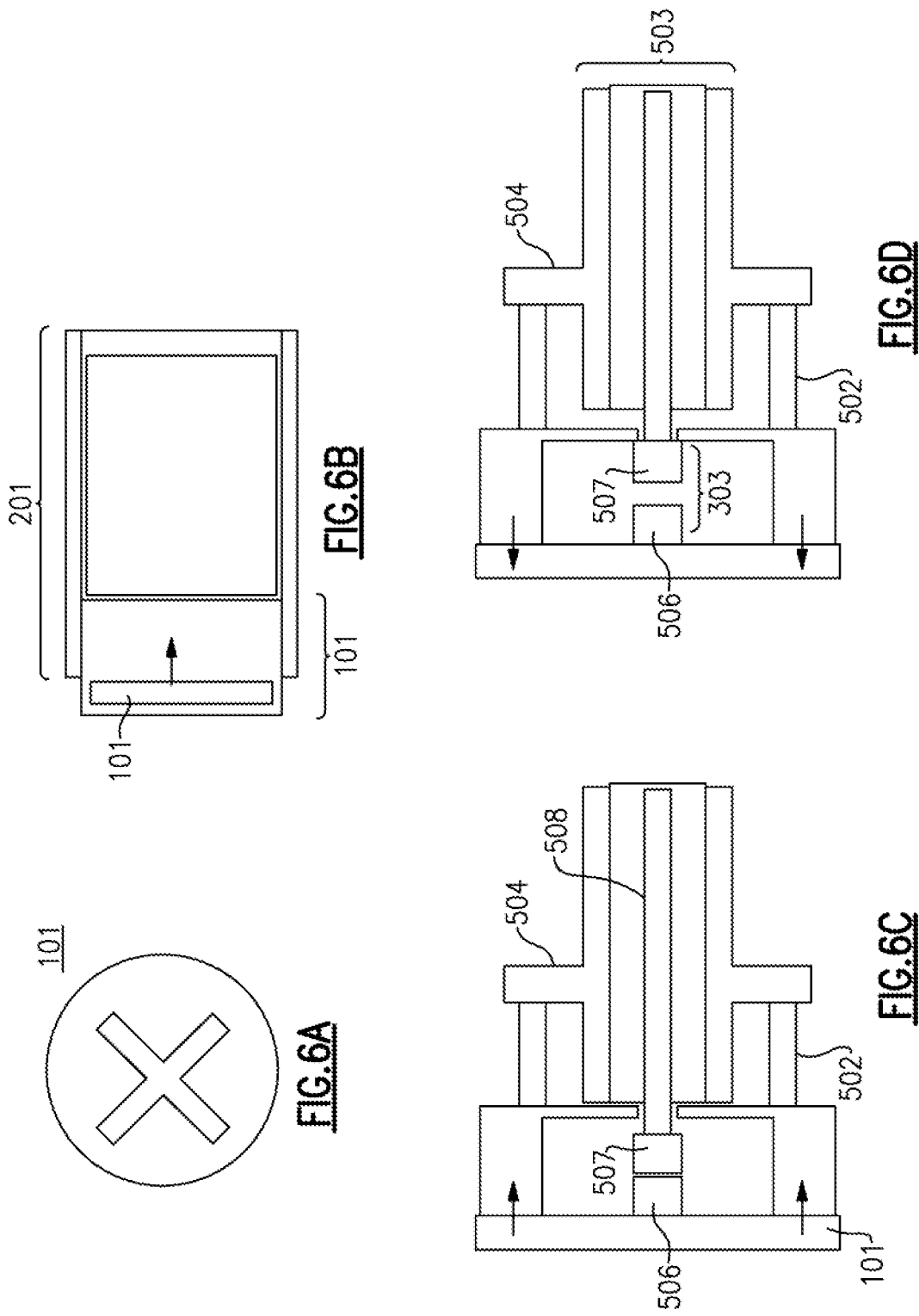

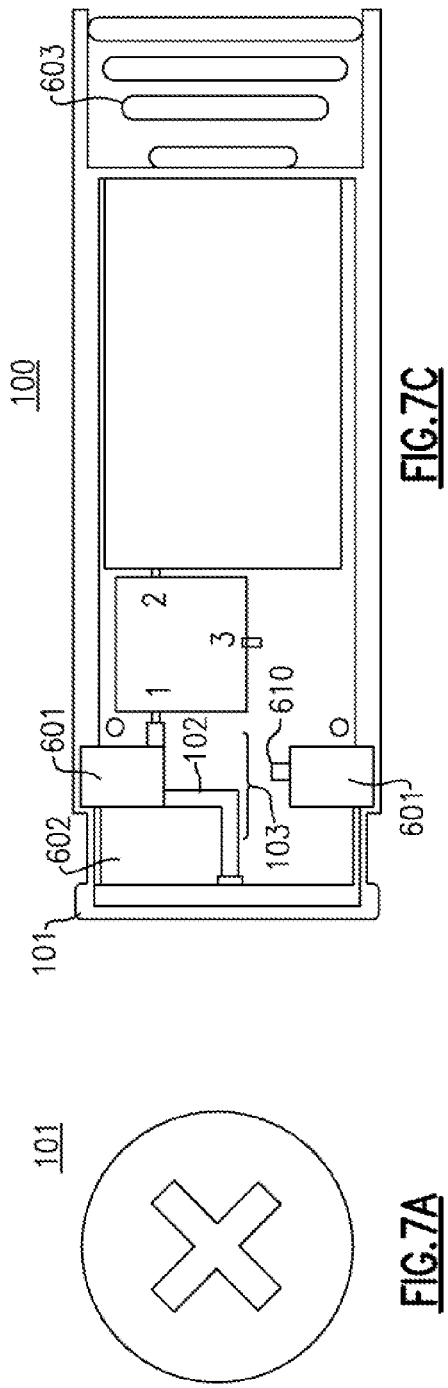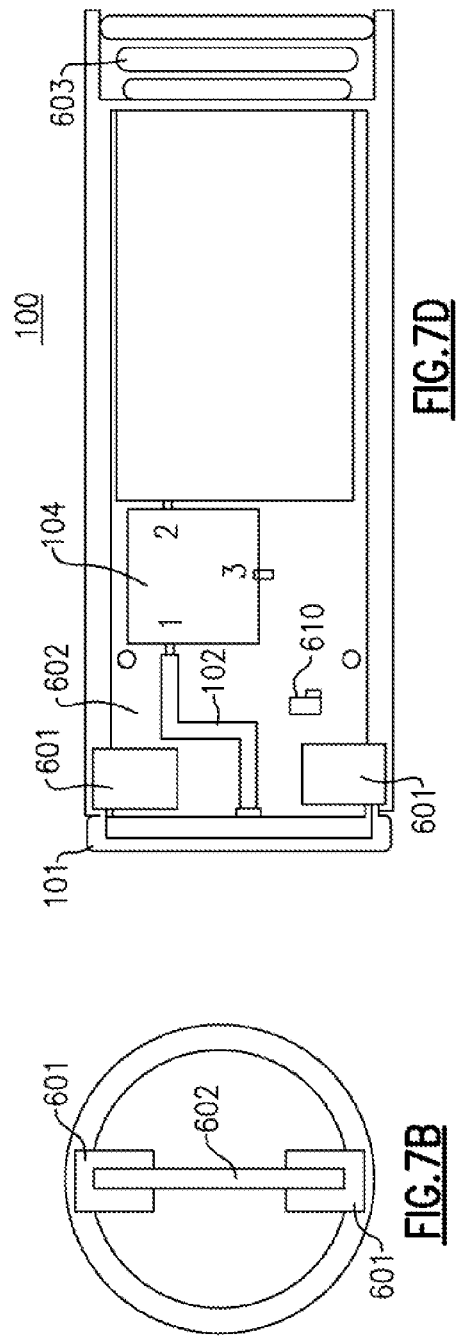

HANDHELD MEDICAL MICROWAVE RADIOMETER

STATEMENT REGARDING FEDERALLY FUNDED RESEARCH OR DEVELOPMENT

The invention described herein was made in the performance of work under a NIH contract NIH/NCRR Grant 2R44RR018024-02A1 (revised), and is subject to the provisions of Public Law 96-517 (35 U.S.C. §202) in which the Contractor has elected to retain title.

FIELD OF THE INVENTION

This invention relates generally to a microwave radiometer and more specifically to a self-calibrating handheld microwave radiometer used to measure subsurface tissue temperature and related aspects thereof.

BACKGROUND OF THE INVENTION

Medical microwave radiometers are instruments that measure thermally generated microwave emissions from subsurface tissues in order to determine the temperature of the tissues. Radiometers can non-invasively measure subsurface tissue temperatures to a depth of several centimeters. By contrast, conventional instruments for measuring subsurface tissue temperatures, such as thermocouple or thermistor thermometers, fiber optic thermometers, etc., each employ an invasive probe that is inserted into the tissues whose temperature is to be measured. Still other known instruments, such as non-invasive IR (infrared) thermometers, measure only skin surface temperature without producing any meaningful information regarding subsurface tissue temperatures. The non-invasive feature of microwave radiometers makes them attractive candidates for measuring subsurface tissue temperatures in a number of medical applications.

One type of microwave radiometer uses the so-called "Dicke" method. The Dicke method causes the input of a microwave receiver to be alternately switched by a Dicke switch at some rate, between a reference noise source and noise which is received by a microwave antenna. A modulator controls both the operation of the Dicke switch and a synchronous detector, which in conjunction with a rectifier forms a synchronous demodulator. One exemplary radiometer using the Dicke method was described by Land in "An efficient, accurate and robust radiometer configuration for microwave temperature measurement for industrial and medical applications", Journal of Microwave Power and Electromagnetic Energy, 36 (3), pgs 139-153, 2001. Land's radiometer connected a main chassis having a microwave switching amplifier by cable to a remote microwave antenna. As is typical of Dicke radiometers, Land's radiometer required synchronous source-reference switching coupled to a synchronous demodulator in the main chassis.

The inventors of the present application, Sterzer and Mawhinney, previously developed a microwave radiometer for the MMTC of Princeton, N.J. FIG. 1 shows a block diagram of one embodiment of the earlier MMTC radiometer, labeled 10. This prior radiometer presented a significant advantage over the Dicke method, in that the synchronous reference-source switching of the Dicke switch or the synchronous demodulator was no longer required. However, the microwave radiometer 10 of FIG. 1 still required five separate microwave switches 62. Beyond a dual temperature reference termination 32 at one port of a circulator 20, the radiometer 10 also had to sequence through two more heated terminations 34, 38 on the antenna side of the reference plane 40, as well as to continuously select between a short 44 at the reference plane 40 and cables to a remote antenna, as well as continuously selecting between a shorted "dummy" cable and the actual microwave signal source from the remote receiving antenna 18. While capable of relatively high performance and used for applications ranging from hyperthermia treatments to basic research in medical radiometry (e.g. as reported by Arunachalam, Sterzer (one of the inventors), et al., in "Characterization of a digital microwave radiometry system for noninvasive thermometry using a temperature-controlled homogeneous test load", PHYSICS IN MEDICINE AND BIOLOGY, Phys. Med. Biol. 53, pages 3883-3901, July, 2008), the radiometer of FIG. 1 is an example of a still relatively complex and expensive medical radiometer instrument.

What is needed, therefore, is a simplified and less costly medical radiometer, which still determines subsurface temperatures, such as, for example, core body temperature, in a reliable and cost effective manner.

SUMMARY OF THE INVENTION

According to a first aspect, there is provided a microwave handheld radiometer for measuring subsurface tissue temperature of a subject, said radiometer comprising a microwave antenna disposed relative to a handheld radiometer housing and adapted to electromagnetically couple to a skin surface of a subject, a circulator having a first circulator input and a second circulator input, the first circulator input being electrically coupled to the antenna via a microwave feedline, a switch electrically disposed between the antenna and a microwave feedline, the switch having a calibrate state and a measure state, a noise source electrically coupled to the circulator, the noise source being configured to provide a first source of thermal noise at a first temperature and a second source of thermal noise at a second temperature and wherein the noise source is switched between the first source and second source upon external command; and a detector creating a detector output.

According to another aspect, there is provided a microwave handheld radiometer for measuring subsurface tissue temperature, said radiometer comprising a microwave antenna means for receiving a microwave electromagnetic signal mechanically disposed at a distal end of said handheld radiometer housing and adapted to electromagnetically couple to a skin surface of a mammal, a circulator having a first circulator input and a second circulator input, the first circulator input electrically coupled to the antenna via a microwave feedline, a switch means for switching between a calibration mode and a measurement mode, a noise source means for generating microwave noise at more than one noise temperature, the noise source electrically coupled to a second input of the circulator, the noise source configured to provide a first source of thermal noise at a first temperature and a second source of thermal noise at a second temperature and wherein the noise source is switched between the first source and second source upon external command; and a detector having a detector output.

According to yet another aspect, there is provided a microwave radiometer system for measuring subsurface tissue temperature, the system comprising a microwave antenna adapted to electromagnetically couple to a skin surface of a mammal, a circulator having a first circulator input and a second circulator input, the first circulator input electrically coupled to the antenna via a microwave feedline, a switch electrically disposed between the antenna and the microwave feedline, a noise source configured to provide a first source of thermal noise at a first temperature and a second source of thermal noise at a second temperature and wherein the noise source is switched between the first source and second source upon external command; a detector having a detector output; and a computer communicatively coupled to a sensor disposed within the radiometer configured to indicate a selected one of 1) the microwave antenna in a measure mode when the switch is sensed to be in the measure state, and 2) the microwave antenna in the calibration mode when the switch is sensed to be in the calibrate state.

The switch used can be a movable mechanical switch in accordance with at least one version of the herein described invention. In another version, the switch can be disposed in terms of software or electrically, such as an FET microwave switch.

An advantage provided by the herein described instrument is a radiometer that is easier and cheaper to manufacture and operate than prior art versions due at least in part to the elimination of cables and related components typically required. In addition, the radiometer is more cost and time effective in terms of its operation but without degradation in reliability thereby enabling accurate readings, for example, of core body temperature of a subject.

These and other advantages and features will be readily apparent from the following Detailed Description, which is to be read in connection with the accompanying drawings.

BRIEF DESCRIPTION OF THE DRAWINGS

FIG. 5A shows an end view of the distal antenna surface of the radiometer of FIG. 4 that makes contact with the skin surface of a patient;

FIG. 5B shows a side view of the antenna of FIG. 5A;

FIG. 5C shows an end view of the proximal side of antenna of FIG. 5A;

FIG. 6A shows an end on view of another X-slot antenna;

FIG. 6B shows a side view of the X-slot antenna of FIG. 6A;

FIG. 6C shows a side view of antenna and switch in a measure position;

FIG. 6D shows a side view of antenna and a switch in a calibrate position;

FIG. 7A shows an end on view of another X-slot antenna;

FIG. 7B shows a proximal view of the antenna of FIG. 7A;

FIG. 7C shows a side view of a radiometer in a calibration position in accordance with an exemplary embodiment of the invention;

FIG. 7D shows a side view of a radiometer in a measurement position in accordance with an exemplary embodiment of the invention;

It should be noted herein that the above-noted drawings are not necessarily to scale, emphasis instead generally being placed upon illustrating the principles of the invention. In the drawings, like numerals are used to indicate like parts throughout the various views.

DETAILED DESCRIPTION

For purposes of the following discussion various terms are used to provide a reasonable frame of reference with regard to the drawings. In addition, Applicant herein specifically makes note of certain terms used throughout this description, as follows:

The term "computer" (e.g. a computer 150 as discussed below) is defined herein as synonymous with microprocessor, microcontroller, and digital signal processor ("DSP"). This term also includes a computer such as a personal computer ("PC"), computer workstation, or an OEM (original equipment manufacturer) computer assembly that includes a microcomputer or microprocessor. It is understood that memory used by the microcomputer, including, for example, microwave radiometer "firmware", can reside in memory physically inside of a microcomputer chip or in memory external to the microcomputer or in a combination of internal and external memory. Similarly, analog signals can be digitized by one or more stand alone analog to digital converters ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. A microwave radiometer having any of the inventive features described herein can operate entirely on one computer, as defined herein, or can include more than one computer.

Figure 1:
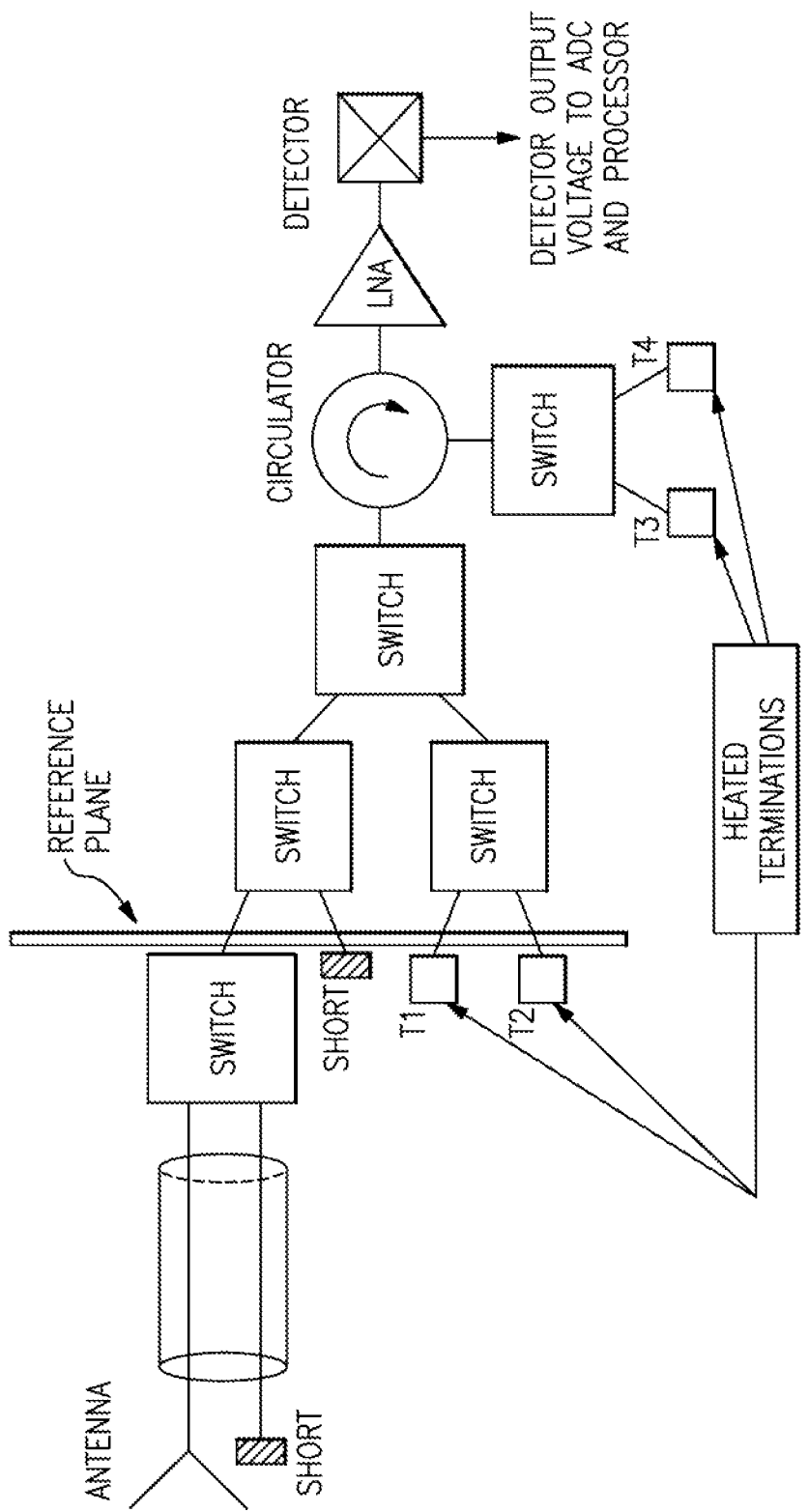
FIG. 1 is a block diagram of a previously known medical microwave radiometer.

By way of background and referring to FIG. 1, a known radiometer is now briefly discussed. This radiometer 10 is configured to include a contact antenna 18, which is connected by a cable 22 to a physically separate low-noise amplifier (LNA) 30 (not shown), detector 50, microcomputer and display (not shown), all of which are contained within a cabinet and operated by a power supply connected to the standard AC mains. This arrangement has an advantage wherein the critical parts of the assembly of FIG. 1 can be temperature controlled because of the readily available electrical power. This chassis-based microwave radiometer 10 also provides sufficient space in the cabinet for a set of relatively bulky low-loss mechanical coaxial switches. A total of five (5) switches 62 are required according to this prior art version for a single frequency model (shown) while seven (7) switches are required for a dual-frequency version (not shown), the latter of which allow for switching between four separate terminations that are set to precise reference temperatures and for switching among the several paths needed for the relatively complex calibration routine necessitated by the interconnecting coaxial cable configuration. Cables of equal type and length are also employed in the calibration routine. One cable 22 carries the temperature related noise from the antenna 18 to the low noise amplifier (LNA) 30 and another cable 23 of exactly equal length and construction is shorted at the end 44. The loss and the effective noise produced by the ambient temperature in which both cables 22, 23 are immersed can then be measured in the shorted cable 23 and are assumed to be the same as from the cable 22 connected to the antenna 18. Although this calibration technique involves additional switching, it provides a means for calibrating both the transfer characteristic of the system (i.e., the relation between the amplified detector output voltage and the temperature and the antenna-to contacting surface impedance match necessary to correct for an emissivity factor (a measure of the effectiveness of transfer of microwave power from the subject to the antenna)).

With the preceding background, the various embodiments of improved radiometer designs, as described herein, eliminate the specific need for microwave cables, as well as the complex switching arrangements that were previously needed during calibration. In the various embodiments that are described herein, both the low noise amplifier (LNA) and detector are incorporated with the antenna in a single common handheld assembly. This combined assembly is made possible by providing a means for shorting out the antenna (or equivalent switching, such as opening the antenna connection) during calibration without need for relatively large microwave switches or active devices that would inherently add conduction noise, and thereby obscure the low level thermal noise measurement.

Figure 2:
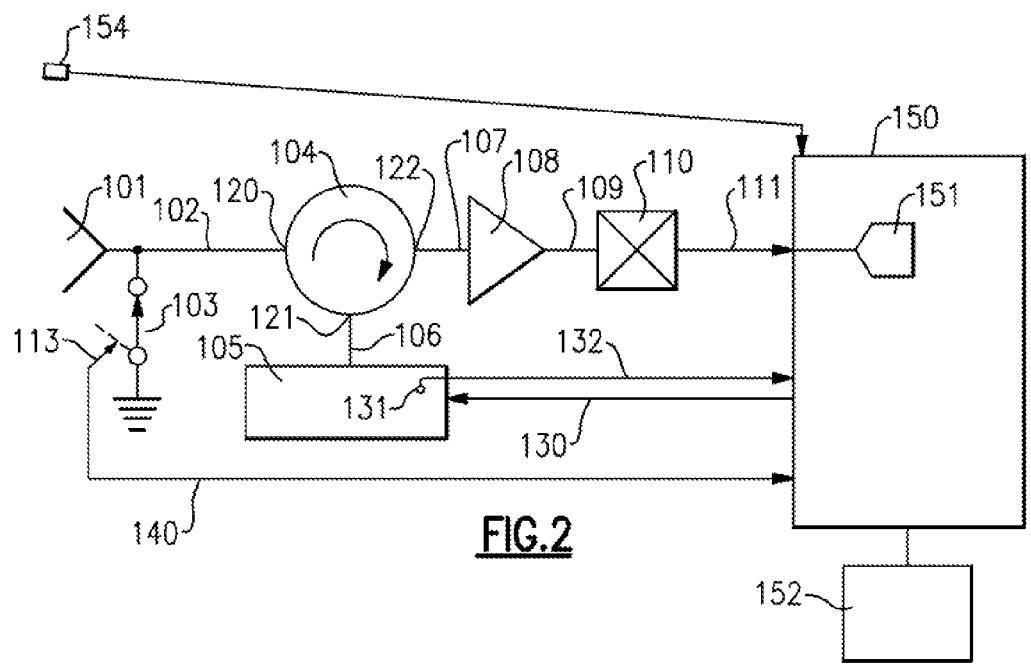
FIG. 2 is a block diagram of one exemplary embodiment of a handheld self-calibrating microwave radiometer.

A handheld microwave radiometer is described in detail, with reference to FIG. 2, which depicts a block diagram of one exemplary embodiment of a self-calibrating medical microwave radiometer that can be used as described herein. More specifically, this specific application is herein described for the purpose of measuring the body core temperature of a subject. It will be readily apparent, however, that other sub-surface tissue temperature effects can be determined in addition to and other than core body temperature such as but not exclusively detecting the presence of inflammations post surgery, appendicitis, growing malignant tumors, and monitoring and controlling therapeutic heating such as hyperthermia, treatments of cancer and thermal ablation of cancers. In this exemplary embodiment, radiometer 100 has been configured for use as a compact handheld instrument depicted in FIG. 2 comprising a plurality of components that are included within a housing including, an analog to digital converter (ADC) 151, a computer 150 providing a control means for the handheld radiometer 100, as described in greater detail below, and a display 152. The computer 150 can include the dedicated control functions, be remote-wired to the radiometer 100 or be resident within the compact housing or casing of the instrument, which as noted also retains the other components. The hand-held radiometer 100 according to this exemplary embodiment is terminated at the distal end of the housing by an antenna 101. Microwave energy in a given frequency band that is received by the antenna 101 is coupled to the distal end of a microwave feedline 102. However, normally-closed switch 103, shorts the distal end of the microwave feedline 102 when in its normally-closed position. Switch 103 can be opened according to this embodiment by mechanical means (e.g., as is shown in various exemplary physical embodiments of handheld radiometer 100 as discussed below). It will be readily apparent that other means, mechanical or other, as described in greater detail below, can be used to short the switch 103, either manually or automatically. According to this embodiment, for example, the normally-closed switch 103 is operated under manual control, also discussed in more detail below.

Microwave energy from the microwave feedline 102 is fed into a first input port 120 of a circulator 104. According to this embodiment, microwave energy from a heated termination 105 is forwarded into a second input port 121 of the circulator 104 over the microwave feedline 106. Microwave energy arriving at an output port 122 of the circulator 104 is forwarded by a feedline 107 as an input to the LNA 108. The LNA 108 amplifies microwave energy in a given frequency band and provides the amplified microwave energy as an output. This output is forwarded over the microwave feedline 109 as an input to a microwave-energy detector 110, such as a Model AD8318 microwave detector from Analog Devices, Inc, which can be tuned to a given frequency band. According to this exemplary embodiment, the detected analog output voltage from the detector 110 is applied over connection 111 as an input to the ADC 151, while the digital output from the ADC 151 is applied as an input to the computer 150, which includes a control means for the radiometer 100 and a connection to an electronic display 152.

In some embodiments, under the control of the computer 150, temperature selection and control commands are applied as an input to the heated termination 105 over a connection 130. The heated termination 105 includes means, such as a thermistor 131, for sensing the actual temperature of heated termination 105. A temperature signal from the heated termination 105 is then applied as an input to the computer 150 over a temperature sensor connection 132. The temperature signal permits the controlled temperature of the heated termination 105 to be set to a particular temperature, such as by means of a closed temperature regulating feedback loop. Also and instead of being held at one particular temperature, the temperature of the heated termination 105 can be switched or adjusted between a lower given controlled temperature (e.g., 35 C.°) and a higher given controlled temperature (e.g., 45 C.°).

A switch signal 113 from the switch 103 can also be applied as an input to the computer 150, such as via a separate connection 140 to inform the computer 150 when the normally-closed switch 103 is closed and when it is open. Not shown in FIG. 2 is a power supply means, typically located exterior of the housing of hand-held radiometer 100, such as a small power supply or via AC power through cabling (not shown) that can be used to power the LNA 108 and the detector 110. Alternatively, power supplied to the LNA 108 and detector 110 can be obtained from batteries (not shown) situated within a compartment (not shown) provided in the compact housing of the handheld radiometer 100. In addition, a thermistor or other sensor 154 is also included to measure skin surface temperature, as described in greater detail in a later section, further provided as input to the computer 150.

Turning now to the operation of the microwave radiometer of FIG. 2, the herein described radiometer 100 remains in a calibration or "calibrate" mode while the switch 103 remains in its normally-closed position, causing the distal end of the microwave feedline 102 to be shorted. In this shorted position, temperature-manifesting microwave energy (i.e. Nyquist noise) from the heated termination 105: (1) enters circulator 104 from its second input port 121; (2) then exits the circulator 104 from its first input port 120, where, after being forwarded to and then being reflected back from the shorted distal end of feedline 102, reenters circulator 104 from its first port 120; and (3) finally exits the circulator 104 via its output port 122. While the radiometer 100 is in the calibration mode, the temperature-manifesting microwave energy exiting circulator 104 from its output port 122, and following amplification by the LNA 108, is detected by the detector 110 to thereby derive a detected-output voltage having an analog magnitude corresponding to the then-existing temperature of the heated termination 105. The analog magnitude of the detected-output voltage from the detector 110, after being digitized by the ADC 151, is applied as an input to the computer 150. Computer 150 also has the actual sensed then-existing temperature of the heated termination 105 applied as an input thereto over connection 132. Thus, so long as the hand-held radiometer 100 remains in its calibration mode, as can be for example, controlled by the sensed-position of switch 103, the computer 150 is programmed to cause the heated termination 105 to be switched or adjusted between two different temperatures (e.g., T1 and T2) corresponding to two input radio frequency (RF) microwave noise voltages (e.g., V1 and V2), with each temperature being held long enough for the temperature sensors and the microwave detector to obtain stable readings that may be related to each other, e.g., T1>V1 and T2>V2, thereby continuing to repeatedly determine the slope and offset of the linear relationship between the digitized magnitude of the detected-output voltage and the heated-termination temperature over a range extending from a lower given temperature (e.g., 35 C.°) and a higher given temperature (e.g., 45 C.°).

Subsequently and in a separate "measurement" or "measure" mode of the instrument, the herein described hand-held radiometer 100 can be used to measure the temperature of a subject, such as the temperature of certain underlying (subsurface) diseased tissue of a patient. In this measurement mode and according to this specific embodiment, the handheld radiometer 100 can be held according to one version with the antenna 101 being maintained substantially in direct physical contact with the exterior tissue of the patient of interest and normally-closed switch 103 is set to its open position, such as by pressing a spring loaded portion of the antenna 101 against a portion of the skin surface of the patient in a specified measurement area (e.g., the forehead, etc.). As a result, the magnitude of the microwave energy in the given frequency band being received by the antenna 101, which is indicative of the temperature of the tissue, is forwarded through the microwave feedline 102 into the first input port 120 of circulator 104, exiting the output port 122 of circulator 104 and then propagated through the feedline 107, LNA 108 and feedline 109 to the input of microwave-energy detector 110. At the same time, temperature-manifesting microwave energy from the heated termination 105, after entering circulator 104 from its second input port 121 and exiting circulator 104 from its first input port 121, travels down the microwave feedline 102 to antenna 101. In the ideal case in which the antenna 101 is perfectly impedance-matched with a patient's tissue being examined, all of the temperature-manifesting microwave energy reaching the antenna 101 will be transmitted into the patient's tissue and none will be reflected back into the circulator 104. However, in the practical case, the antenna 101 is less than perfectly impedance-matched with patient's tissue being examined. Therefore, some of the temperature-manifesting microwave energy reaching the antenna 101 from the heated termination 105 will thus be reflected. This (1) reflected temperature-manifesting microwave energy, combined with the (2) temperature-manifesting microwave energy received by antenna 101 from the patient's tissue being examined, enters the first input port 120 of circulator 104 and then exits the output port 122 of circulator 104. This combined temperature-manifesting microwave energy, after being amplified by the LNA 108, is applied as an input to the detector 110. The analog magnitude of the detected-output voltage from detector 110, after being digitized by ADC 151, is applied as an input to the computer 150 over the connection 111.

Microwave energy traveling in circulator 104 suffers losses. The losses suffered by the microwave energy from the heated termination 105 exceed the loss suffered by the microwave energy from antenna 101 by the loss suffered in traveling from the second input port 121 to the first input port 120 of circulator 104. This latter loss is pre-measured and stored by the computer 150. The computer 150 is configured to run a stored algorithm that employs this stored loss data, together with the above-described calibration-mode and measurement-mode stored data, in order to digitally compute the temperature of the patient's tissue being examined. The digitally-computed temperature can be displayed on the display portion of computer 150 (e.g. on display 152) and/or stored in memory for later use.

The principle of operation of the calibration-mode and measurement-mode in accordance with this embodiment is now described in greater detail. As compared to the prior art microwave radiometer of FIG. 1 and as previously noted, the improved compact radiometer 100, by incorporating the LNA and the detector into the antenna assembly (e.g. FIG. 2 or FIG. 4), eliminates the need for microwave cables and complex switching arrangements. This improvement is due in part to the herein described means for shorting the antenna during calibration without the use of large microwave switches or active devices that inherently add conduction noise, thereby obscuring the desired low level thermal noise measurement.

Referring to FIG. 2 and in the normal shorted position, thermal noise from the heated termination 105 is reflected from the short back through the circulator 120 to the LNA 108 and the detector 110, thereby providing a detected output voltage that is proportional to the temperature of the termination 105. The computer 150 sets at least two different temperatures and reads the actual values from a temperature sensor which is thermally coupled to the termination 105 in order to establish the slope and offset of the voltage vs. temperature characteristic ("T-V") of the radiometer 100. The two temperatures can also be produced by toggling between two different input voltages with each held long enough for the temperature sensors, and the microwave detector to obtain stable readings that may be related to each other, e.g., T1 and V1 and T2 and V2. By leaving the switch 103 in the shorted position, the handheld radiometer 100 can be continuously updating the T-V calibration and ready to use for temperature measurement as soon as the short is removed by activating the manual or automatic shorting mechanism. Note that continuous calibration eliminates most of the significant waiting time that was inherent in prior art radiometers, such as the radiometer shown in FIG. 1.

To enter the measurement mode, switch 103 is placed into the non-shorting condition, either manually or automatically, wherein the noise from the antenna traverses the same path as the calibration signal through the circulator 105 to the LNA 108 and the detector 110, thereby providing a detected output voltage that can be related to temperature using the determined calibration factors. A correction can be made for the small and pre-measured loss of the calibration signal for the one section of the circulator through which the antenna signal does not pass. Additional calibration is corrected for any impedance mismatch between the antenna 101 and the target, usually human or animal tissue. This additional calibration can be accomplished after the sensitivity correction is established with the switch 103 in the non-shorting position, once again, either under computer control or by the continuous toggling, changing the temperatures of the heated termination. For example, if there is no change in the detector output with the two different temperatures all of the thermal noise must have been delivered via the antenna and absorbed by the target tissue, indicating a perfect match between the antenna and the surface of the skin and requiring no correction. Conversely, if the detector voltage changes as much as it had with the short in place, the impedance match is very poor and the reading is indeterminate. With intermediate values of detector voltage difference, between perfect antenna coupling to the skin surface giving total reflection and full loss with total absorption, an algorithm running on computer 150 can calculate and apply the proper emissivity (antenna coupling coefficient) correction for the temperature measurement.

Figure 3A:
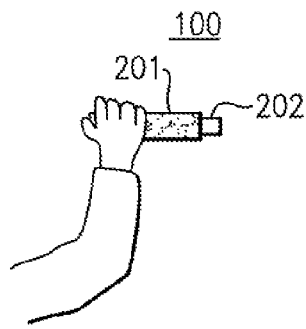
FIG. 3A depicts a user holding the handheld microwave radiometer of FIG. 2.
Figure 3B:
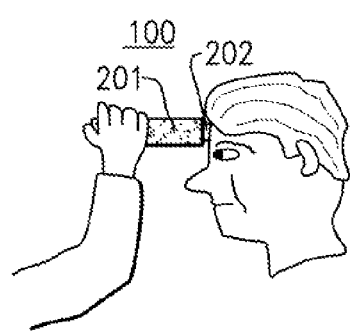
FIG. 3B depicts a user holding the handheld microwave radiometer of FIG. 2 against a skin surface of a patient.

FIG. 3A depicts the above-first described hand-held microwave radiometer 100 in use, the radiometer being defined by a cylindrical or tubular housing 201 and having a spring-loaded antenna section 202. In the embodiment of FIG. 3A, antenna section 202 is shown in an extended position (i.e., antenna in a "released" position) where as described above, the switch 103 is in a normally closed position shorting the distal end of the microwave feedline 102 to a ground, placing the instrument in its calibration-mode (input to radiometer 100 is shorted). According to this embodiment, the radiometer 100 is placed in the measurement mode when the radiometer 100 is pressed against a patient and the spring-loaded antenna section 202 is compressed, mechanically causing the switch 103 to open. FIG. 3B illustrates a user holding the hand-held microwave radiometer 100 of FIG. 3A in direct physical contact against a skin surface of a patient, causing the spring loaded antenna section 202 to be compressed and shifted axially (antenna in a patient contact position) into the confines of the cylindrical housing 201, wherein the normally-closed switch 103 is caused to open thereby removing the ground connection to the distal end of the microwave feedline 102 and allowing signals to propagate both to and from antenna 101, as described above. As noted above, the switch can also be opened electrically and can be opened either manually or automatically.

Now turning in more detail to the switch near antenna 101, such as for example, switch 103 (FIG. 2), there is near total reflection of signals present on microwave feedline 102 when the normally-closed switch is closed shorting the distal end of microwave feedline 102 to a ground. As has been described above, this near total reflection provides information that allows the radiometer 100 to self-calibrate when not pressed against the skin of a patient (e.g., FIG. 3A). In other embodiments, another way to achieve substantially the same near total reflection from the distal end of the radiometer 100 is to cause an open circuit near the distal end of microwave feedline 102, e.g. when the instrument is not being pressed against the skin of a patient (FIG. 3A).

Figure 4:
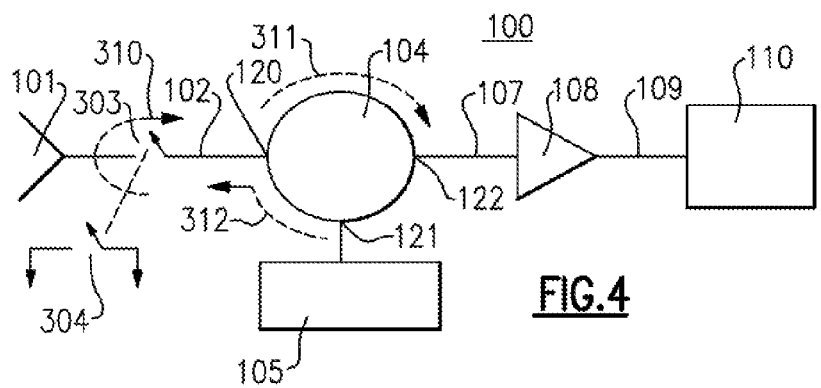
FIG. 4 is a block diagram of another exemplary embodiment of a self-calibrating radiometer using a transmission line "open" for calibration.

FIG. 4 shows a block diagram of another exemplary embodiment of a microwave radiometer 100. Similar components used in previous embodiments are labeled with the same reference numerals for the sake of clarity. According to this embodiment, the radiometer 300 includes a normally-open switch 303 which causes an open circuit near the distal end of the microwave feedline 102 when the instrument is in the calibration mode. In this embodiment, when radiometer 300 is not pressed against a skin surface of a patient (e.g. FIG. 3A), switch 303 is in the normally-open position. As explained above, this open circuit provides the same near total reflection when the switch 103, FIG. 2, is in a normally-closed position. The position of switch 303 can be sensed and conveyed to a computer 150, for example, by a position indicating switch 304. When the radiometer 100 is pressed against the skin surface of a subject to make a measurement (e.g. FIG. 3B), normally-open switch 303 closes, thereby connecting antenna 101 to the microwave feedline 102.

EXAMPLE

Figure 5D:
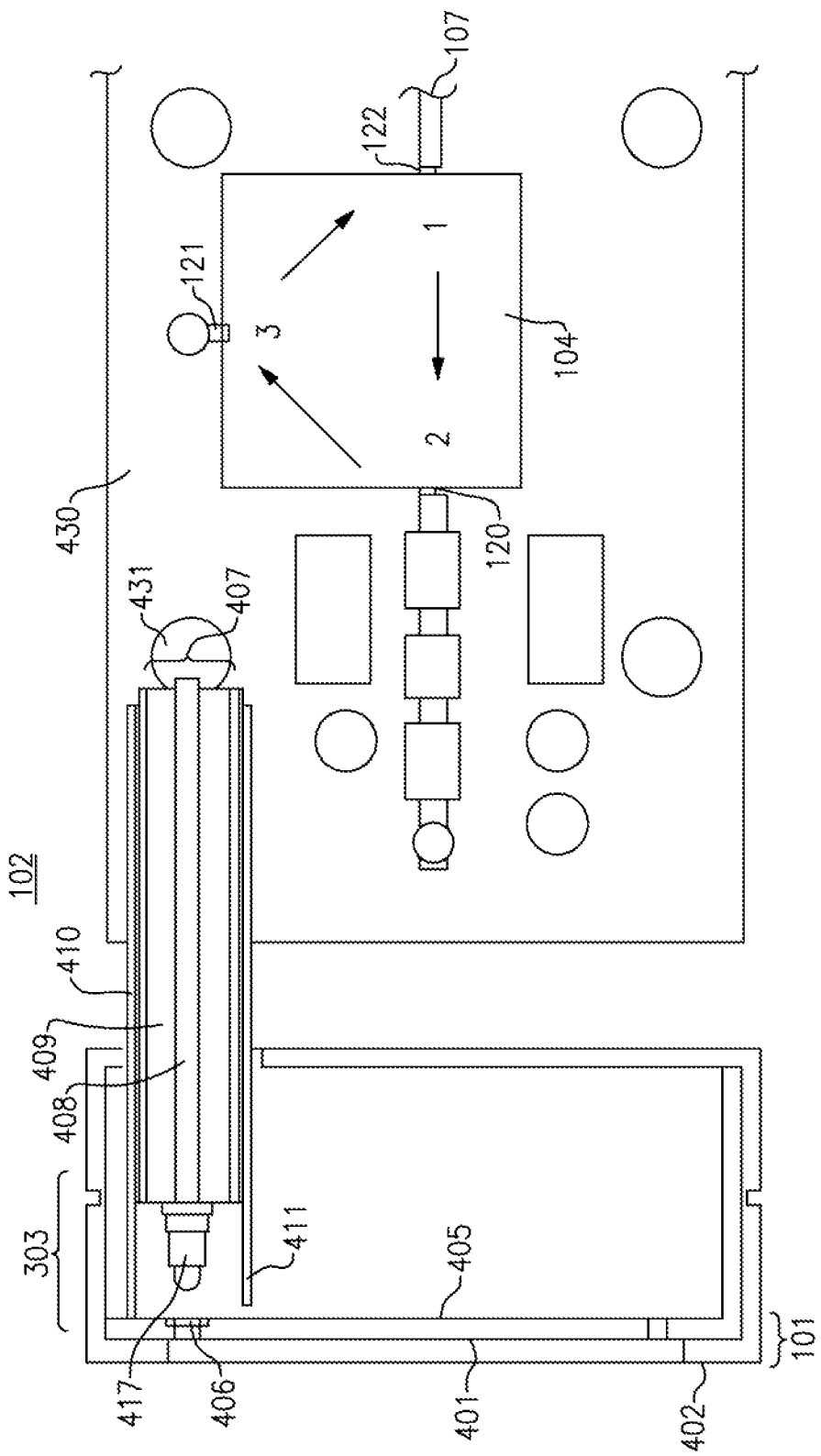
FIG. 5D shows a side view of one embodiment of an antenna, switch, sliding transmission line, and radiometer circuit board.

FIG. 5A through FIG. 5F depict an exemplary radiometer 400 including an antenna 101, a switch 303, and a microwave feedline 102 according to the normally-open switch 303 embodiment of FIG. 4. FIG. 5A shows an end view of an antenna surface that makes contact with the skin surface of a patient (the distal end of a microwave radiometer 100). According to this exemplary embodiment, the antenna 101 is an "X slot" antenna. The slot for the formed "X" is defined by a metal surface 402, such as can be formed from brass or any other suitable metal conductor, metal film, or other suitable metal deposit, having an "X" shaped cutout, shown as slot 412. Adjacent to the "X" shaped cutout slot 412 is a dielectric material 401. One exemplary dielectric material 401 suitable for use in an antenna 101 is a ceramic composite substrate, such as the RT/duroid 6010LM microwave laminate manufactured by Rogers Corporation of Chandler, Ariz.

FIG. 5B shows a side view of the antenna 101 of FIG. 5A and switch 303. The assembly of FIG. 5B is roughly analogous to the spring-loaded antenna section 202 of FIG. 3A and FIG. 3B. Note that in the example, spring loaded antenna section 202 can include a larger diameter outer shroud (not shown) overlaying an equivalent cylindrical housing 201, i.e., spring loaded antenna section 202 can have either a smaller diameter than cylindrical housing 201 as shown in FIG. 3A and FIG. 3B, or a larger diameter than a cylindrical housing 201. The section of microwave feedline 102 shown in FIG. 5B is a coaxial structure 407 including an outer shielding conductor 410, a dielectric 409, and a center conductor 408. Outer shielding conductor 410 can be fabricated from any suitable metal, such as brass. Dielectric 409 can be any suitable dielectric such as air or foam, to give the desired characteristic impedance for microwave feedline 102.

In the embodiment of FIG. 5B, the illustrated section of the microwave feedline 102 can be seen to slidingly engage the antenna 101 via a tube 411 having a slightly larger inner diameter than the outer diameter of outer shielding conductor 410. Tube 411 can also be fabricated from any suitable metal, such as brass. An opening 416 in tube 411 provides a clearance for the "X slot" antenna electrical connection via an antenna feed connection 405. Feed connection 405 is a conductor running along the surface of dielectric material 401 opposite to the surface of dielectric material 401 that is adjacent to metal surface 402. Contact 406 provides one contact of the switch 303, which allows spring loaded contact 417 to electrically couple to the antenna feed connection 405, such as when spring loaded antenna section 202 is pressingly engaged against the skin surface of the patient according to this embodiment.

FIG. 5C shows an end view of the surface of dielectric material 401, which is opposite to the surface of dielectric material 401 that is adjacent to and supported by metal surface 402. Feed connection 405 runs or extends along the surface of the dielectric material 401. Also visible in FIG. 5C is a contact 406 of the switch 303.

FIG. 5D shows a side view of antenna 101, switch 303, and a radiometer circuit board 430 (cylindrical housing 201 (FIG. 3A) not shown). Note that there can be an additional shroud as part of spring loaded antenna section 202 (FIG. 3A)). In the view of FIG. 5D, the sliding engagement action of the forward section of the microwave feedline 102 nearest to the antenna 101 can be seen. In this example, the coaxial structure 407 including an outer shielding conductor 410, can be seen as sliding within tube 411 as described above. Note that tube 411 and circuit board 430 remain stationary with regard to cylindrical housing 201, FIG. 3A, (not shown) when the spring loaded antenna section 202, FIG. 3A, including antenna 101 is pressed in. Contact 406, which provides one contact of switch 303, allows spring loaded contact 417 to electrically couple to the antenna feed connection 405. Note that this forward section of the microwave feedline 102 can terminate into circuit board 430 by use of any suitable interface connector or soldered connection in order to properly match coaxial structure 407 to a microwave stripline (not shown) on circuit board 430 which couples the forward section of microwave feedline 102 into the stripline so as to electrically couple the signals from the distal end of sliding microwave feedline 102 the rest of the way to circulator 104.

Figure 5E:
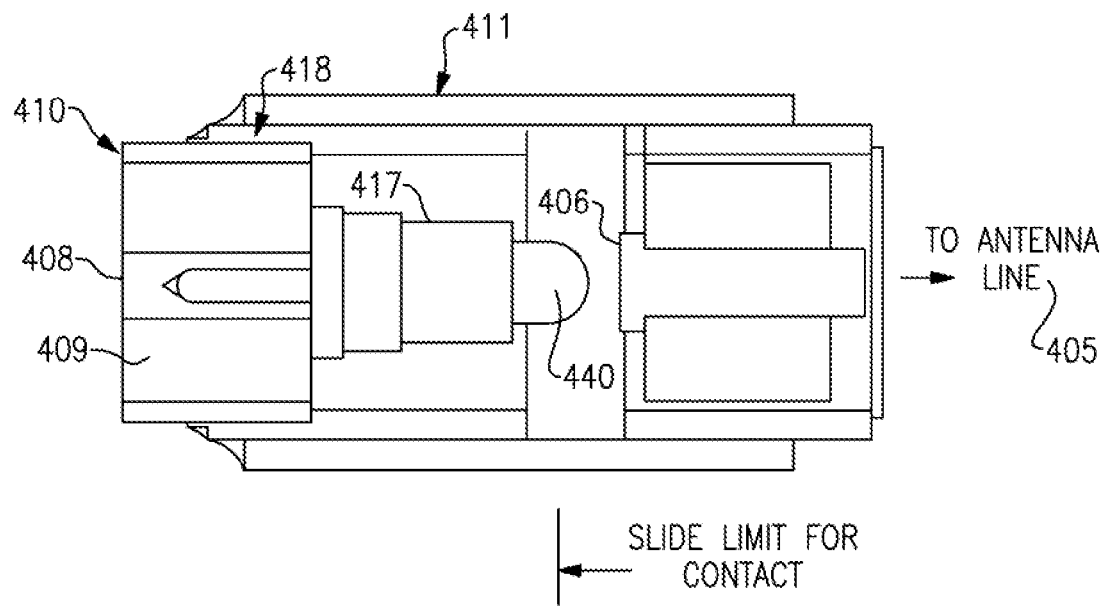
FIG. 5E shows a more detailed side view of the switch of the radiometer shown in FIG. 5D.

FIG. 5E shows a more detailed side view of the switch 303 of the radiometer 100 shown in FIG. 5D. In FIG. 5E, it can be seen that there can be an additional stop tube 418 to create a mechanical back stop so that when spring loaded portion 440 of spring loaded contact 417 advances towards contact 406, stop tube 418 mechanically limits the travel of coaxial structure 407 before the spring-loaded portion 440 of spring loaded contact 417 completely "bottoms out". According to this exemplary embodiment, the coaxial structure 407 has an outer diameter of about 0.141", stop tube 418 is fabricated from brass tubing having an outer diameter of about 5/32", and tube 411 is fabricated from brass tubing having an outer diameter of about 3/16".

Figure 5F:
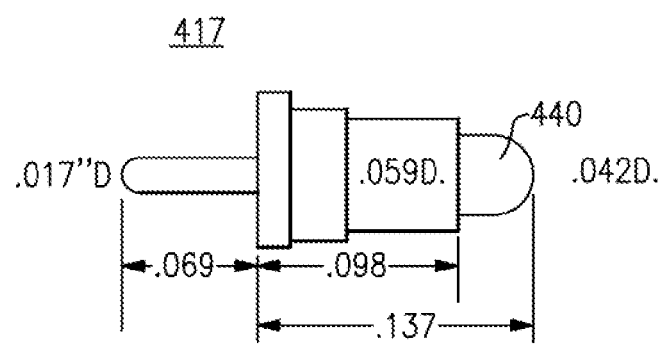
FIG. 5F shows a detailed side view of the spring loaded contact of FIG. 5E.

FIG. 5F shows a detailed side view of the spring loaded contact 417 used in a prototype. This spring loaded contact 417 is part no. 0906-0-15-20-70-14-11-0 available from the MILL-MAX Manufacturing Corporation of Oyster Bay, N.Y. or other suitable spring-loaded contact.

Figure 5G:
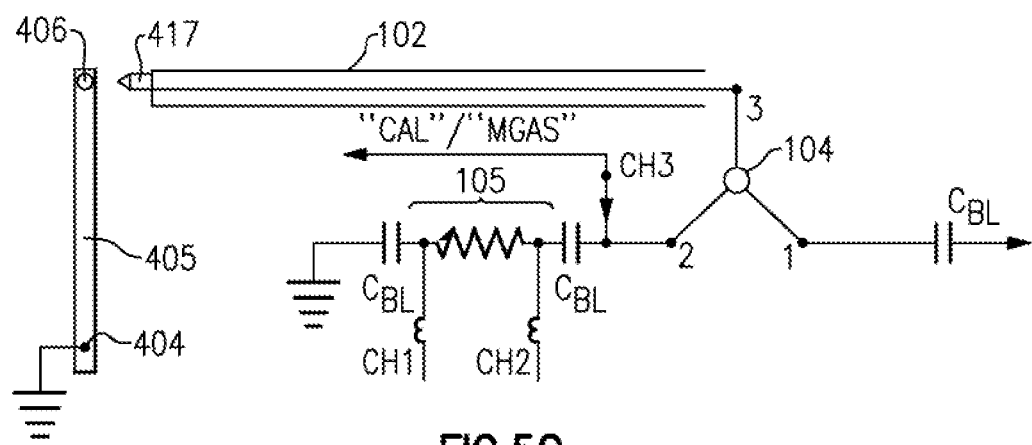
FIG. 5G shows an equivalent circuit of one embodiment of a radiometer according to FIG. 5D.

FIG. 5G shows an equivalent circuit diagram of one embodiment of a radiometer according to FIG. 5D. According to this embodiment, two circuit functions are performed by switch 303, namely an RF microwave connection of antenna 101 FIG. 5D to the circulator 104 and a "DC" switched connection to serve the function of switch 303 position (i.e. open in a calibrate position, or closed in a measure position). The principle of operation of the embodiment is that a "closed" DC connection from common 404 through feed connection 405, contact 406, spring loaded contact 417, microwave feedline 102, and choke CH3 indicates to a circuit connected to handheld radiometer 100 that the radiometer is pressed against the surface of a patient and in a measurement mode. Opening of the same DC path indicates that the instrument is in a calibration mode. Note that the microwave RF path from feed connection 405 via microwave feedline 102 to circulator 104 is substantially unaffected by the DC path because of the presence of blocking capacitors $C_{BL}$ and choke CH3. Note also, that common 404, which is always present at one end of feed connection 405 of antenna 101, does not short the microwave RF signal received by the antenna 101 (not shown) and propagated along the microwave feedline 102 to the circulator 104 when the radiometer 100 is in a measure mode. Chokes CH1 and CH2 serve a similar function of separating a DC path from the RF microwave path, but for a different reason. Chokes CH1 and CH2 are related to a DC heating current for the heated termination 105.

Figure 5H:
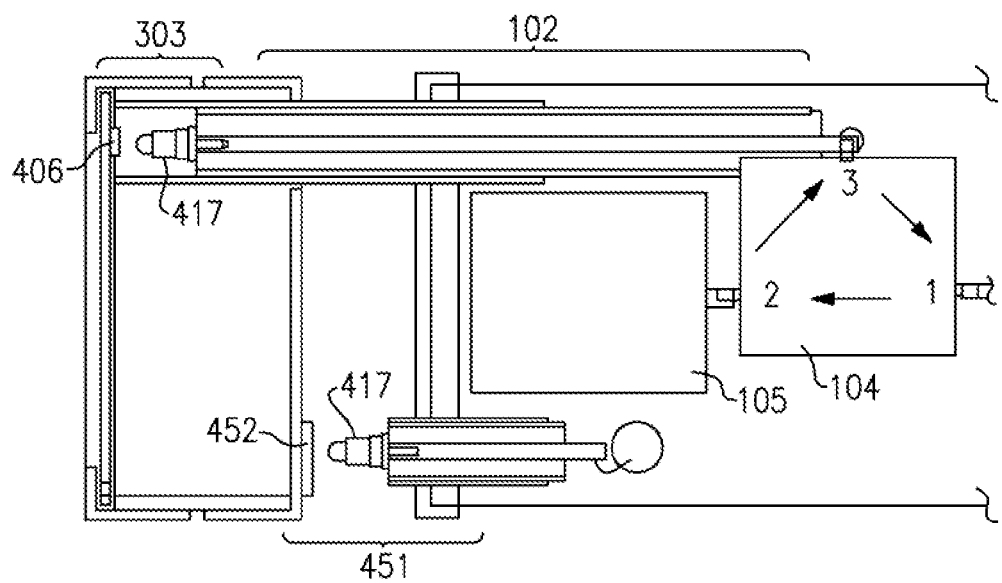
FIG. 5H shows another embodiment of a radiometer further including second switch as a position sensor.

FIG. 5H shows another embodiment of a radiometer 100 in which the functions of switch 303 and switch position sensor 304 have been separated into two physically distinct separate switches. In this embodiment, switch 303 is provided by contact 406 and spring loaded contact 417 as described above. An additional switch 451 having a contact 452 and a second spring loaded contact 417 provide the function of switch 304 to indicate to a connected computer when the radiometer 100 is in a calibrate mode (e.g. FIG. 3A) and when the radiometer 100 is in a measure mode (e.g. FIG. 3B). Note that such embodiments having two separate switches trade off ease of signal isolation (isolation of microwave RF path from the DC mode indicator) for a somewhat increased mechanical complexity.

Another embodiment of a radiometer 100 with a normally-open switch 303 is shown in FIGS. 6A-6D. FIG. 6A shows an end on view of another X-slot antenna 101. FIG. 6B shows a side view of the X-slot antenna 101 of FIG. 6A relative to the cylindrical housing of the hand-held radiometer. In FIG. 6B, it can be seen that spring-loaded antenna section 202 can be axially translated into the confines of the cylindrical housing 201 when pressed against a subject, as previously shown in FIG. 3A and FIG. 3B. FIG. 6C shows a side view of antenna 101 and switch 303 in the measurement position (i.e., radiometer 100 pressed against the skin surface of a patient (not shown in this view)). When antenna 101 is pressed into radiometer 100, spring 502 is caused to compress, allowing coaxial structure 503 to slide within the support 504. Contact 506 on antenna 101 comes in contact with contact 507 of coaxial structure 503, causing the center conductor 508 of coaxial structure 503 to be electrically coupled to antenna 101. FIG. 6D shows a side view of antenna 101 and switch 303 in a calibration position (i.e., radiometer 100 not pressed against a patient). In this position, the spring 502 is relaxed as coaxial structure 503 is shown in a retracted position with the contact 507 moved away, causing switch 303 to be in an open position. Note that the above embodiment has been illustrated in a simplified form. For example, there can be additional mechanical guiding mechanisms (not shown), such as support 504 and/or spring contacts analogous to spring loaded contact 417 of FIG. 5F and/or mechanical stops (not shown).

Another embodiment of a radiometer 100 with a normally-closed switch 103, FIG. 2, is shown in FIGS. 7A-7D. FIG. 7A shows an end-on view of a X-slot antenna 101. FIG. 7B shows a view of antenna 101 from a side opposite to the side that can be pressed against a subject. In this embodiment, a circuit board 602 is slidably movable within slots 601 (e.g., "U" shaped metal guides) when the radiometer 100 is placed into direct physical contact against the skin of the subject. Slots 601 can be formed from a metal conductor or include an inner conductive surface through which circuit board 602 slides. FIG. 7C shows a side view of the radiometer 100 in the calibrate position (i.e., not pressed against a patient). In this position, spring 603 is shown in a relaxed position and circuit board 601 extends the antenna 101 out from cylindrical housing 201, FIG. 3A. Switch 103 includes slot 601 which is fabricated from a conductor, such as brass. Circuit board 602 slides between a calibrate position (spring 603 relaxed) and a measure position (spring 603 compressed). In the calibrate position (FIG. 7C), switch 103 is in the closed position, shorting microwave feedline 102 (here a strip line on circuit board 602) to ground. In the measure position (FIG. 7D), switch 103 is in the open position, not shorting microwave feedline 102 (here a strip line on circuit board 602) to ground. This embodiment can be improved by use of sliding spring contacts (not shown) for engaging the strip line of microwave feedline 102 and/or mechanical stops (not shown). One of the slots 601 can also serve as a contact (FIG. 7C, FIG. 7D) to provide a position sensing indicator (independent of the microwave RF path).

Figure 8A:
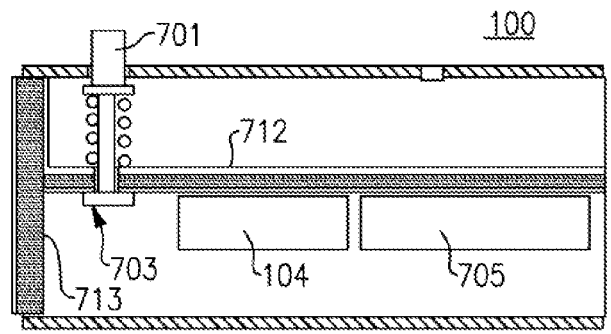
FIG. 8A shows a side cutaway view of a radiometer having a pushbutton 701 shown in a normally-closed position in accordance with another exemplary embodiment.
Figures 8B, 8C:
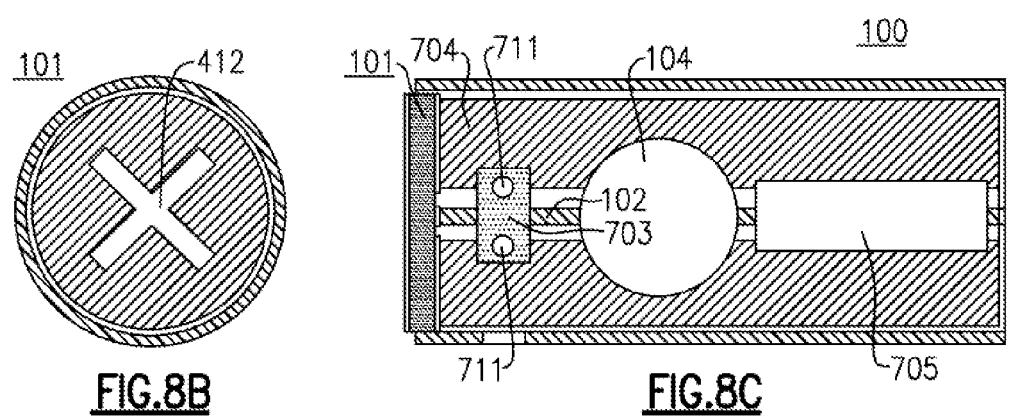
FIG. 8B shows an end view of an X-slot antenna suitable for use with the radiometer of FIG. 8A.
FIG. 8C shows a top cutaway view of the radiometer of FIG. 8A.
Figure 8D:
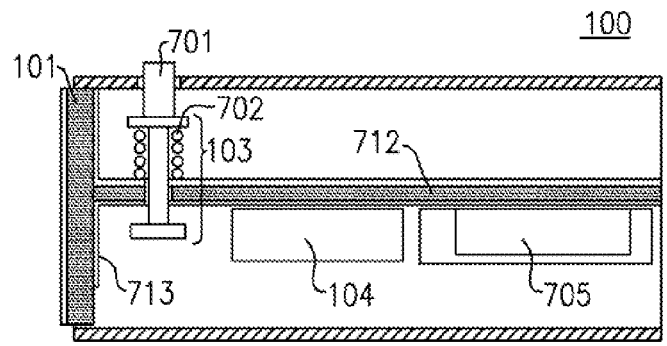
FIG. 8D shows a cutaway side view of the radiometer when the pushbutton is depressed in accordance with the embodiment of FIG. 8A-8C.

FIG. 8A to FIG. 8D show an embodiment of a finger-operated mechanism (a pushbutton 701). FIG. 8A shows a side cutaway view of radiometer 100 having pushbutton 701 shown in a normally-closed position (spring 702 relaxed). Block 705 represents various radiometer electronic components mounted on a circuit board 712. FIG. 8B shows an end view of an X-slot antenna 101 suitable for use with the radiometer 100 of FIG. 8A having a slot 412 and antenna feedline 713. FIG. 8C shows a top cutaway view of the radiometer 100 of FIG. 8A. When switch 103 is in the normally-closed (calibrate) position, conductive bar 703 places a removable short on a microstrip line 102 by causing a short to nearby conductive ground plane sections 704. In one embodiment of the switch 103, a conductive bar 703 attached to a pair of parallel dielectric rods 711 that go through the substrate, can be pulled against the substrate by extension springs that are mounted around guide rods. This places a short across the input to the radiometer receiver and enables the receiver to be calibrated by reflecting known noise signals into the receiver in the manner previously described. FIG. 8D shows a cutaway side view of the radiometer 100 in which the pushbutton 701 is depressed, placing radiometer 100 into a measure mode. When the pushbutton 701 is pushed, spring 702 compresses and the conductive bar 703 is lifted away from microstrip line 102 putting the receiver into the "measurement" mode. Correction for any antenna mismatch is made as the first step in this mode by determining the ratio of the difference produced by the two different termination temperatures in the measure mode and the difference in the calibrate mode.

Figure 10:
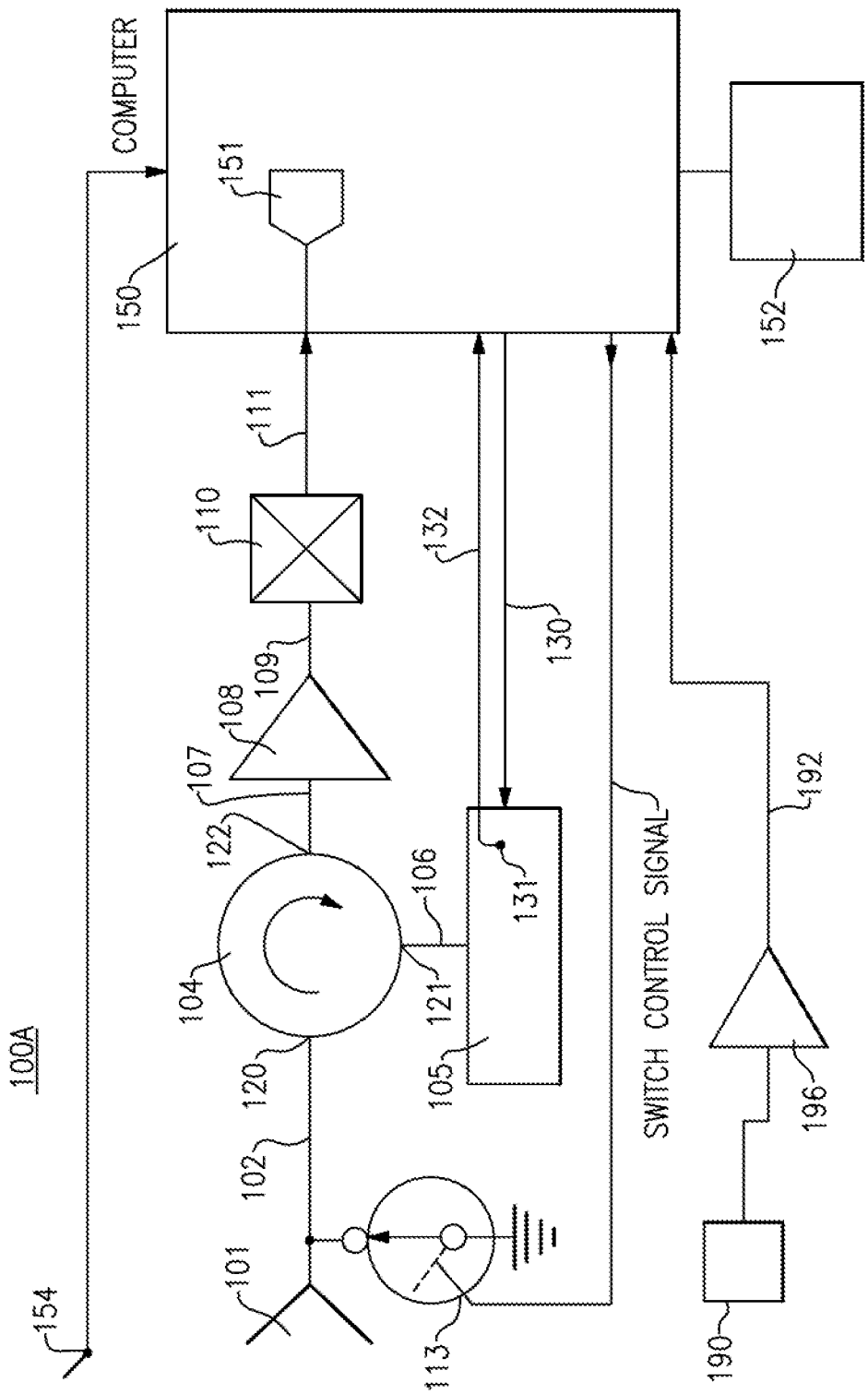
FIG. 10 depicts a block diagram of another hand-held self calibrating radiometer in accordance with another exemplary embodiment of the present invention.

Each of the preceding embodiments of the handheld radiometer requires physical direct contact between the microwave antenna and the skin surface of the patient. Other variations, however, are possible. By way of example and referring to FIG. 10, another version of a handheld radiometer can include means in which the switch is caused to be automatically closed. Primarily, this embodiment is somewhat similar to that described according to FIG. 2 and the same reference numerals are used for similar components for the sake of clarity. That is, the radiometer 100A includes an antenna 101 having a microwave feedline 102 extending to the input end 120 of the circulator 104, the circulator having an output port 122 further extending to an integrated LNA 108 via feedline 107, A second input port 121 is connected by means of a microwave feedline 106 to a heated termination 105. The LNA 108 amplifies microwave energy in a given frequency band and provides the amplified microwave energy as an output forwarded over feedline 109 to a detector 110, which can be tuned to a given frequency band. Voltage from the detector 110 is applied over the connection 111 as an input to an ADC 151, applied as an input to a computer 150, which includes a control means for the radiometer 100A and a connection to an electronic display 152. Temperature and control commands are applied as an input to the heated termination 105 over a connection 130, wherein the heated termination includes a thermistor 131 or other similar means for sensing the actual temperature of the heated termination 105. In this embodiment, a shorting switch 113a is opened and closed by electric control as opposed to relying upon contact by the antenna 101 as in the preceding versions. More specifically, at least one proximity or non-contact sensor 190 is arranged in combination with the switch 113a, wherein a signal 192 is emitted by the sensor based on the distance between the skin surface of the subject and the hand-held housing, which is received as input by the computer 150, the signal being appropriately conditioned by means of a circuit 196. When a threshold signal (distance) has been reached or exceeded by the proximity sensor 190, the switch 113a can be opened electrically, permitting the radiometer 100a to automatically be switched from the calibration mode to the measurement mode, for measurements of subsurface temperature in the manner previously described.

Figure 19:
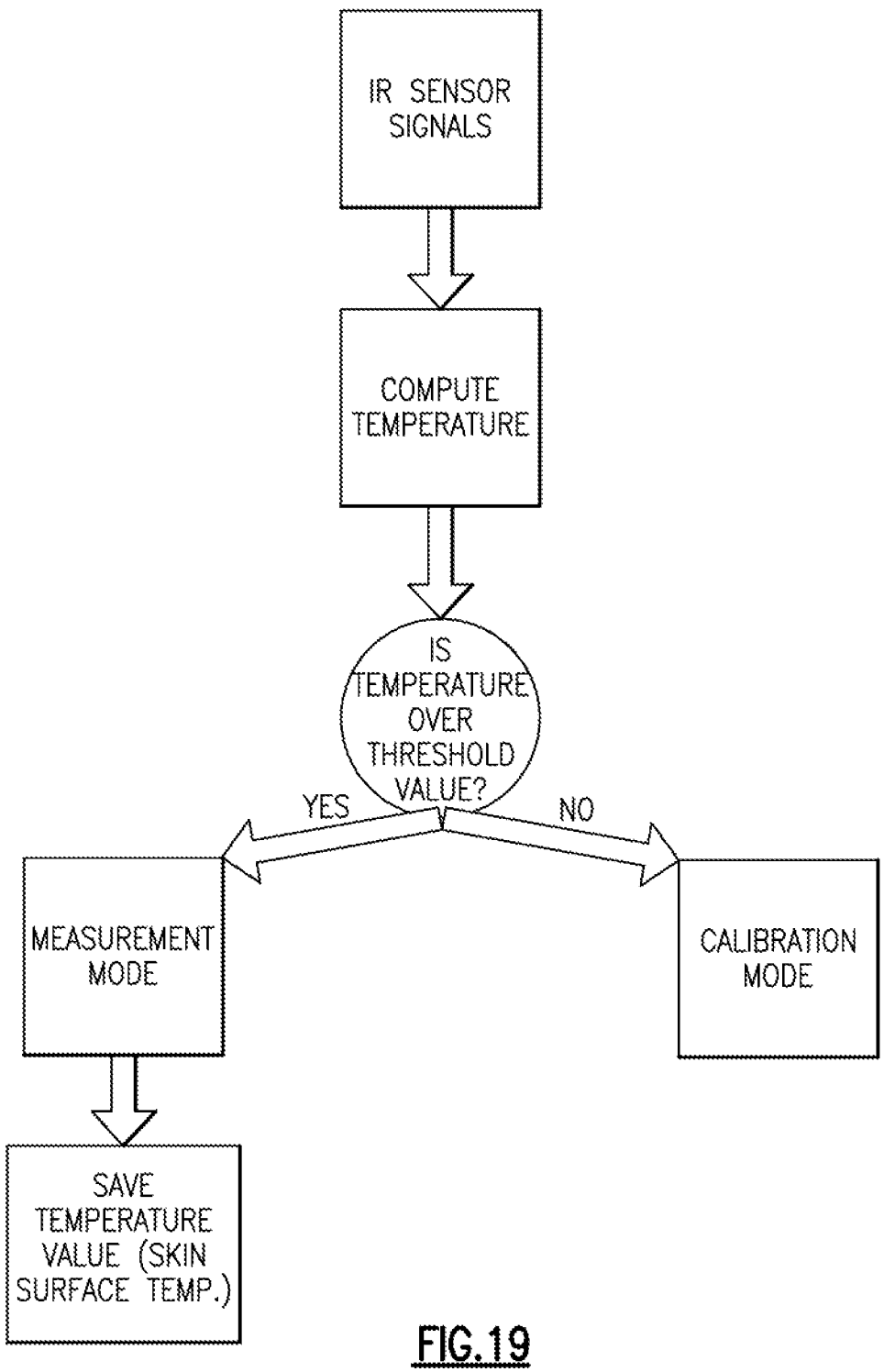
FIG. 19 illustrates a flow chart relating to the use of a surface temperature measuring sensor in relation to the operation of the herein described microwave radiometer.
Figure 20:
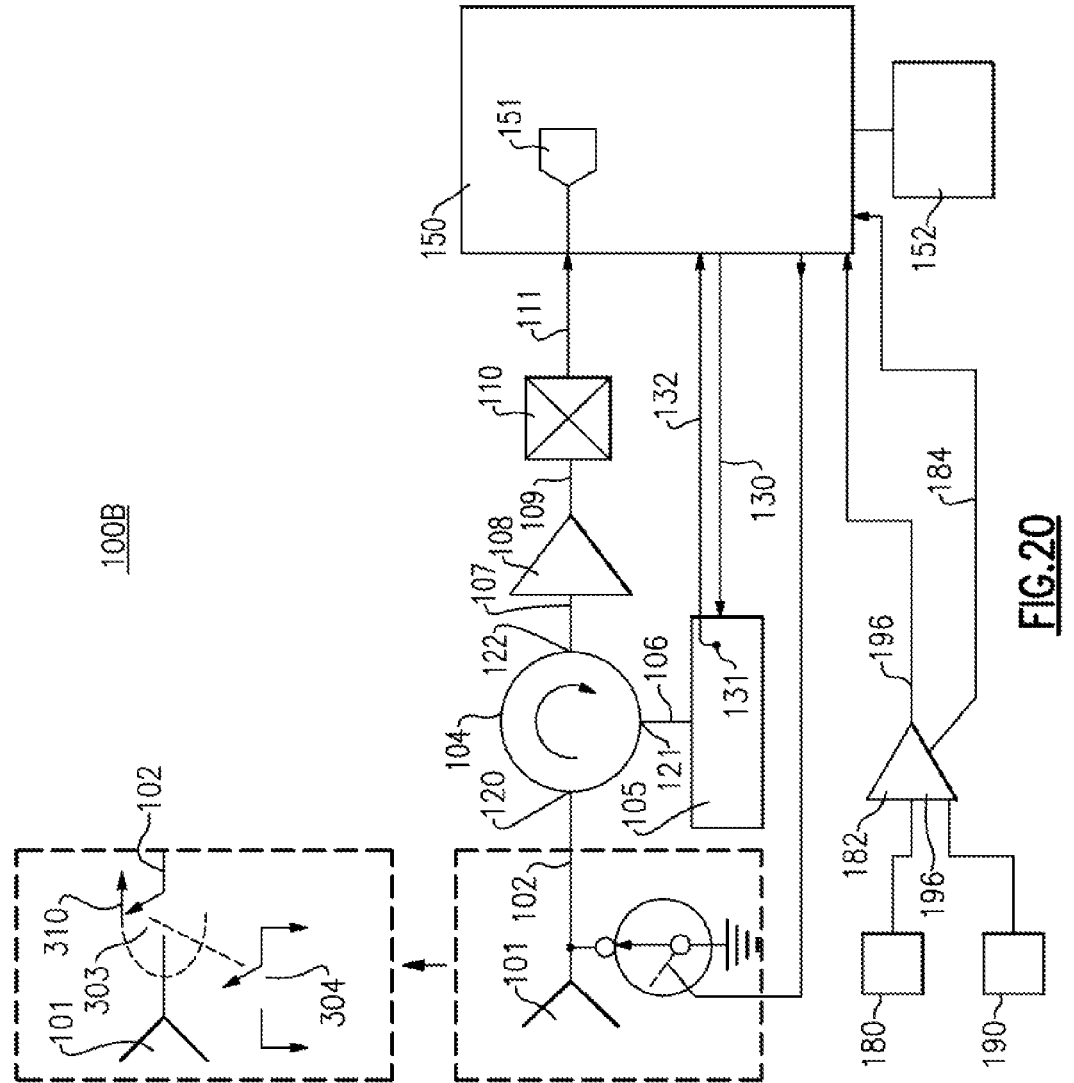
FIG. 20 depicts a hand-held radiometer in accordance with another exemplary embodiment.

A hand-held radiometer according to a similar version can also include at least one temperature sensor in order to measure surface effects. According to one alternative embodiment for radiometer 100B, see FIGS. 19 and 20, an IR temperature sensor 180 can be disposed in relation to the radiometer 100B at one distal end thereof can be electrically connected to the proximity sensor 190 and the computer 150 or alternatively a thermistor or similar measuring sensor used to measure skin temperature. According to this version, and referring to FIG. 20, the proximity sensor 190 provides a threshold signal to the computer 150 as input, indicative of a specific distance wherein the IR sensor 180 can be enabled; that is, energized. According to at least one version of the herein described radiometer, the IR sensor 180 can be initially preheated by means of a heater element (not shown) disposed in relation to the IR sensor, such as a thermistor, when a first predetermined distance is reached or alternatively when the radiometer is activated. Pre-heating permits the IR sensor 180 to reach the predetermined temperature in a faster time interval for measurement (such as the body temperature of a subject). According to the flowchart of FIG. 19 and if the IR sensor 180, FIG. 20, provides a threshold measurement and the radiometer is within a specific distance from the skin surface of the subject, the radiometer is automatically switched from the calibration mode to the measurement mode using switch 113a and the skin surface temperature reading determined by the IR sensor is stored by the computer 150. If the threshold reading is not sufficient, the radiometer 100B is maintained in the calibration mode.

Figure 9:
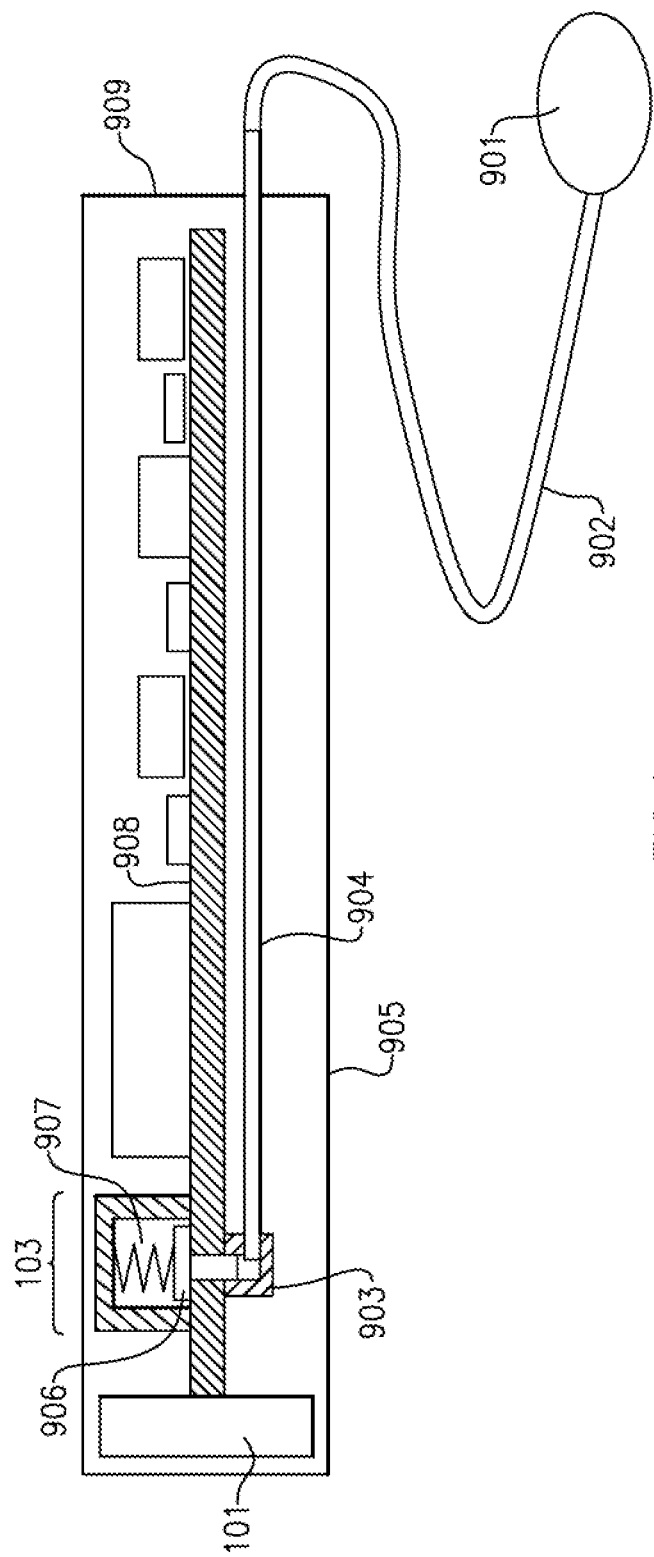
FIG. 9 shows a drawing of a bulb-operated radiometer in accordance with yet another exemplary embodiment of the invention.

In terms of other variations, FIG. 9 illustrates a bulb-operated radiometer 100. In this embodiment, a pneumatic mechanism allows for remote operation of the radiometer shorting switch 103 (FIG. 2). In this embodiment, the remote actuation uses air pressure generated by a rubber bulb 901, such as the type used on a blood pressure mechanism, to push a miniature piston 903 so as to interrupt the mechanical contact between the microstrip line and the metallic ground as made by movable conductive bar 906, thus placing the instrument into the measure mode. One advantage is that relatively large electromechanical mechanisms are not required. The actuating line 902 can be very small and flexible allowing its use in long catheters, and it can easily be operated either by a hand or a foot pedal arrangement (not shown). The above mechanism or similar embodiments can also be arranged to operate in the opposite manner where the instrument is placed into the calibrate mode (switch 103 closed) when the bulb is squeezed.

Figure 10A:
FIG. 10A shows a helical microwave antenna in a measurement position.
Figure 10B:
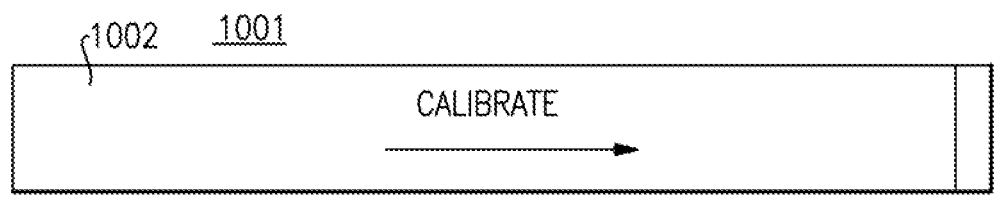
FIG. 10B shows the helical microwave antenna of FIG. 10A in a calibrate or sheathed position.
Figure 10C:
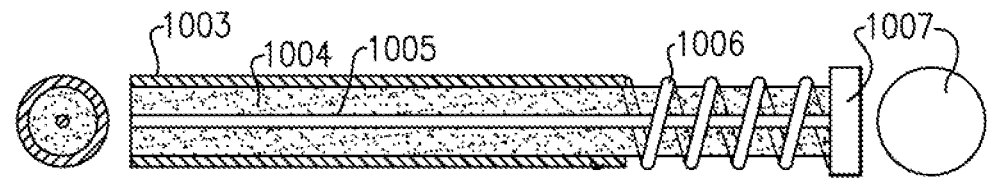
FIG. 10C shows a more detailed view of the helical microwave antenna of FIG. 10A.
Figure 10D:
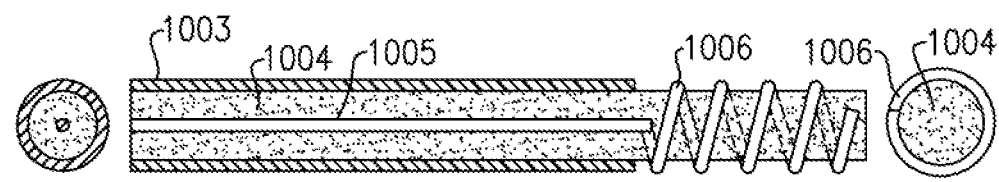
FIG. 10D shows another embodiment of a helical microwave antenna.
Figure 10E:
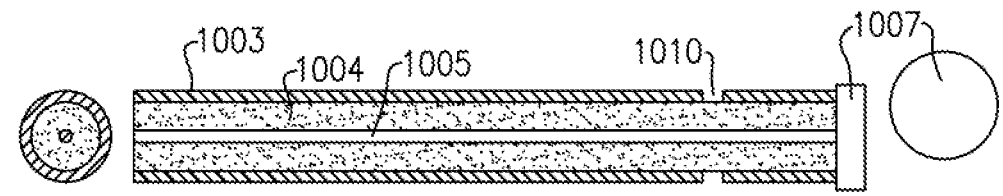
FIG. 10E shows a cylindrical microwave slot antenna having a slot.

For applications where there is insufficient room to include some or all of the microwave components as for intra-vessel or channel treatments (such as in veins, a urethra, or a rectum) or when the antenna has a dual or multiple purpose such as hyperthermia or similar microwave therapies, a relatively small thin antenna can be used. FIG. 10A to FIG. 10E depict one embodiment of relatively small thin cylindrical antennae suitable for measurements within a channel in a body. More specifically, FIG. 10A shows a helical microwave antenna 1001 in a measure position (antenna 101, FIG. 2) having a movable shielding sheath 1002. FIG. 10B shows the helical microwave antenna 1001 of FIG. 10A in a calibrate or sheathed position where the helical microwave antenna 1001 is substantially completely shielded by the movable shielding sheath 1002. FIG. 10C shows a more detailed view of helical microwave antenna 1001 and a forward section of microwave feedline 102. As in other embodiments described above, microwave feedline 102 includes an outer shielding layer 1003 surrounding an intermediate dielectric 1004, the latter of which surrounds a center conductor 1005. Towards the distal end of microwave feedline 102, and past a section of outer shielding layer 1003, a helical winding 1006 of the helical microwave antenna 1001 is wound on a section of intermediate dielectric 1004. Helical winding 1006 is electrically coupled to an end cap 1007 at the distal end of helical microwave antenna 1001. The end cap 1007 is also electrically coupled to the center conductor 1005. In the embodiment of FIG. 10C, the sheath 1002 is extended to cover helical winding 1006 and makes electrical contact between the sheath 1002 and end cap 1007, providing a short between the center conductor 1005 and ground (FIG. 10B) to place the radiometer in a calibrate mode (switch 103, FIG. 2 closed). When the sheath is retracted, the short is removed and the helical winding 1006 is exposed (FIG. 10A), placing the instrument in a measure mode (switch 103, FIG. 2 open). FIG. 10D shows another embodiment of a helical microwave antenna 1001 where instead of achieving the removable short through an end cap (FIG. 10C), a short is removably made by the outer surfaces of helical winding 1006 coming in electrical contact with an inner conductive surface of sheath 1002 when it is extended over helical winding 1006 (calibrate mode). FIG. 10E shows a cylindrical microwave slot antenna having a slot 1010. In this embodiment, when extended fully over slot 1010, an end cap 1007 creates a short to the sheath 1002 (calibrate mode). Sheath 1002 and/or antenna 1001 sliding action can be controlled either manually or by mechanical or pneumatic actuators or any other suitable mechanism which can extend or retract the metal sheath 1002. There can also be an extension tab (not shown) connected to either sheath 1002 or microwave feedline 102 at a proximate location to cause sheath 1002 to slidingly engage antenna 1001 in a covered and shorted position (calibrate mode) or in an open exposed position (measure mode). Note that there are other variations by which a finger operated button can be used to remove or create the short. For example, the short circuit could be a forked bar that is "pushed" free of the line from a spring-loaded side-mounted plunger (not shown). A slide switch arrangement (e.g. as is common in flashlights) is also be feasible.

Returning now to the heated termination 105 (FIG. 2), as described above, the heated termination 105 (effectively, a calibrated microwave noise source) is toggled between two different temperatures (e.g. T1 and T2) corresponding to two microwave noise voltages (e.g. $V_N1$ and $V_N2$). In most embodiments of a handheld radiometer 100, the block labeled heated termination 105 toggles back and forth between two temperatures, thus providing two distinct and pre-defined microwave noise voltage levels to a port of the circulator (e.g. circulator 104, FIG. 2). While in many embodiments the two temperatures are "pre-defined", note that because the calibration process (calculation of offset and gain in the calibrate mode, typically followed by calculation of the antenna coupling coefficient core temperature in the measure mode) is generally done with averaging and for concurrent measurements, absolute stability of the reference noise voltages (e.g. $V_N1$ and $V_N2$) is not needed.

A heated termination 105 having two temperatures to generate two distinct microwave noise voltages can be made in several ways. Since a resistor can be used as a thermal noise source according to the well known Nyquist equation, a single resistor can be operated at two different temperatures. Or, there can be two separate resistive noise sources and an RF switch that toggles between them. Such resistive structures and switches need be constructed according to known microwave construction techniques in order to not inadvertently substantially limit the bandwidth of the generated noise in the microwave band being used by the radiometer.

Another aspect of heated termination 105 is that where the temperature is varied, to achieve a reasonably steady desired temperature over a time span compatible with the cycling of the calibration and measure modes of the radiometer. Where heating is provided by a fixed current or voltage, typically temperature rise and fall follows an exponential curve similar to RC charging of a resistor and capacitor. A rate of rise of temperature (T) versus time (t), dT/dt, can be forced (e.g. for a faster temperature rise) with a momentary higher voltage or current, however such "open-loop" forcing can be less accurate and result in excessive temperature over-shoot. Where one resistive element is cycled between two temperatures, a closed loop temperature controller can provide sufficient speed and accuracy to toggle between the two desired temperatures. One advantage of using a single resistive element (toggled between two temperatures) is that since there is one single microwave path (not switched), the termination presents a substantially constant impedance to a circulator 104, FIG. 2.

Where a resistive element is heated above ambient temperatures, thermal isolation (thermal insulation) of the resistive element can limit undesired heat loss to surrounding structures. Further, regarding thermal isolation, there are competing electronic concerns. For example, there should be an adequate RF common connection to the ground plane of a circuit board. Also, unless active cooling techniques are employed, where one or more resistive elements are operated between two temperatures, there must also be a thermal discharge path for passive cooling. Thus, in some such embodiments an adequate amount of heat sinking should be used.

EXAMPLE

A termination resistor was electrically connected to a ground plane. Since it was physically connected directly to ground, there was a heat sink in the thermal path through the ground connection. Yet, some control of the amount of heat sinking was needed to balance un-desired heat loss during heating, against desired heat loss to cool to a desired lower temperature during a cooling cycle to a lower desired temperature over the two temperature toggle cycle. To determine this balance point, a nominally 50 ohm resistor was centrally mounted on a 0.5 inch long short microstrip line and shorted to ground at one end with an SMA connector at the other end for connection to a circulator. By measuring the through-loss in the reverse direction, the circulator isolation allowed the quality of the termination to be determined. Four (4) different types of 50 Ohm chip resistors were tested. From this testing, it was determined that the quality of the overall termination was relatively poor when the resistors were grounded through approximately 0.2-inches of copper line by using a layer of somewhat thermally isolated electrically-conductive tape as a ground patch at the end of the resistor. Because conductive tape, such as copper foil tape, is very thin, it has relatively poor thermal conductivity to a substrate (e.g. a circuit board) and can be used to replace direct grounding, such as soldering to a ground plane, where thermal isolation is needed to balance the heating/cooling cycle of a termination.

Figure 11:
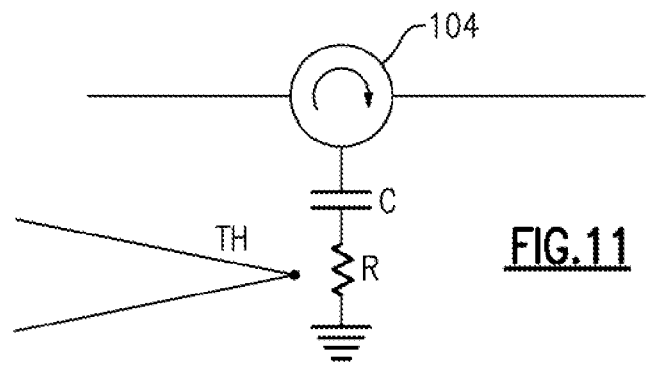
FIG. 11 shows a schematic diagram of a partially completed radiometer sensor assembly used in temperature testing.

FIG. 11 shows a schematic diagram of a partially completed radiometer sensor assembly used in temperature testing. The termination R was a directly-heated 51 ohm resistor (part no. ERJ-6GEYJ510, such as available from Panasonic of Kyoto, Japan). A thermistor TH was placed in thermal contact with termination R. A wideband capacitor (such as is available from Dielectric Laboratories, Inc of Cazenovia, N.Y.) was used to couple the microwave RF noise signal into circulator 104. The heating voltage was electrically coupled to R via a microwave choke (not shown). The termination R was heated from about 35° C. to about 46° C. in about 1 second and cooled back to about 35° C. in 2 seconds. In this exemplary test, a radiometer using a 5 second toggle period was contemplated. It is believed that these times can be significantly shortened by improving the thermal paths.

EXAMPLE

Figure 12:
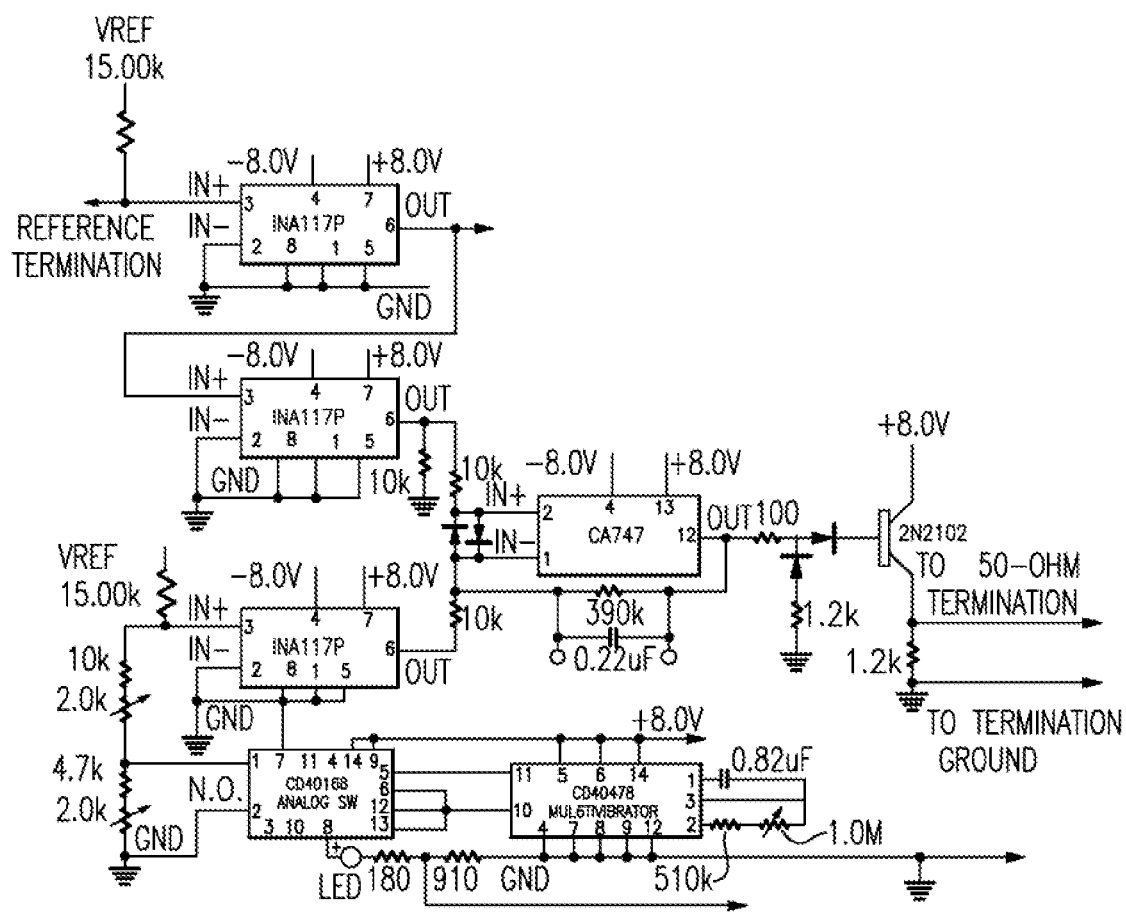
FIG. 12 shows a schematic diagram of one exemplary embodiment of a closed loop temperature controller.

FIG. 12 shows a schematic diagram of one exemplary embodiment of a closed loop temperature controller useful to set the temperature of a heated termination 105 for a radiometer application. In the exemplary temperature controller of FIG. 12, a free-running multivibrator toggles analog switch open and closed. The analog switch alternately shorts out resistors in reference voltage path causing the reference voltage to alternate between the two desired values. Voltages from termination-mounted thermistors and the switched references are applied to an op-amp. An error voltage output drives a transistor emitter follower which powers the resistive termination to control its temperature between two alternating values.

In another embodiment, field effect transistors (FET) can be used as the heated resistive elements for a heated termination 105, FIG. 2. For example, two small FET devices can be used as controllable resistances (but, not in a typical FET circuit topology, where dc or ac voltages applied to the drain) to provide a microwave noise source having the desired two reference temperatures. Each FET can be heated by intimate contact with a heater such as a chip resistor used as a heater. These heater resistors are not in the microwave circuit and can be of any convenient value so that when the available voltage is applied, the resulting current flow through each resistor causes the temperature of each respective FET to be raised to the desired temperature to provide the desired noise power reference. Such resistive heating of FETs can be accomplished either by open-loop or closed-loop means to bring and maintain each FET at the desired temperature. A temperature sensor, such as a thermistor or thermocouple, can be used to monitor the temperature for measurement and/or for temperature control purposes.

When the heated FETs are connected to provide a path from drain to source, they function as resistors with values that depend upon their size and the applied gate voltage. For example, NEC L-devices typically have a through resistance of about 5 ohms with no voltage applied to the gate. With a bias of negative 1.0-Volt or greater applied to the gate, the resistance increases to thousands of ohms essentially creating an open circuit. A specific selected bias voltage can set the FET resistance to any value in between including 50 ohms (approximately −0.6 volts) which can be used to properly terminate the respective circulator 104 port that is electrically coupled to the heated noise source 105. Note that a shunt inductance can be included to resonate out the shunt capacitance of the FETs leaving only the 50 ohms resistance as the termination.

Figure 13A:
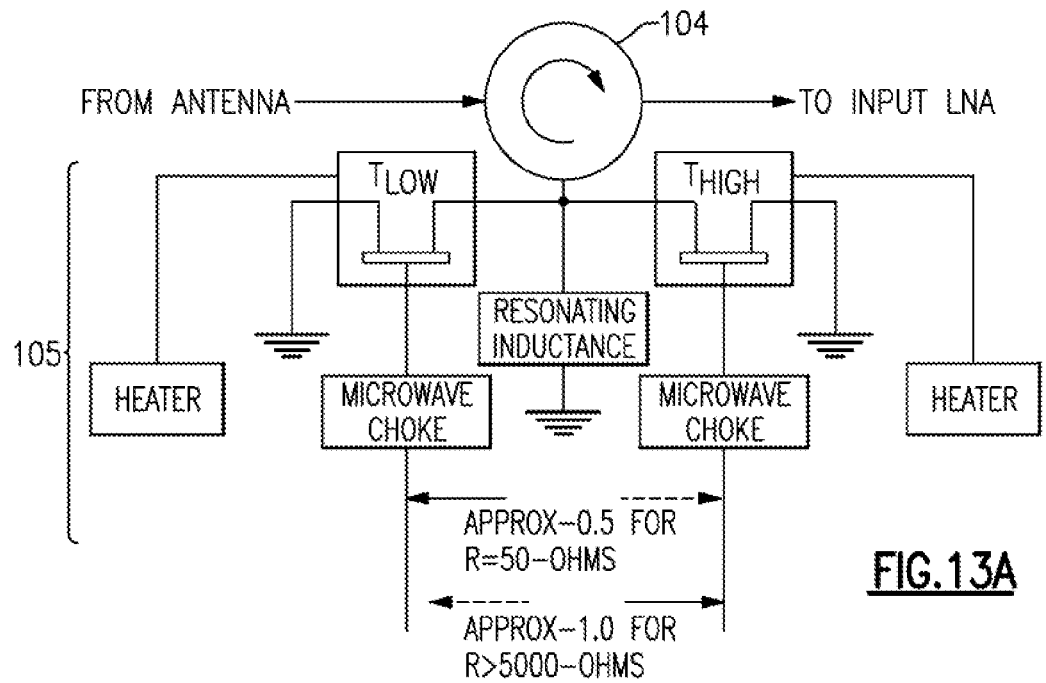
FIG. 13A shows a block diagram of one embodiment of a parallel arrangement of conductive FETs used as a microwave noise source.
Figure 13B:
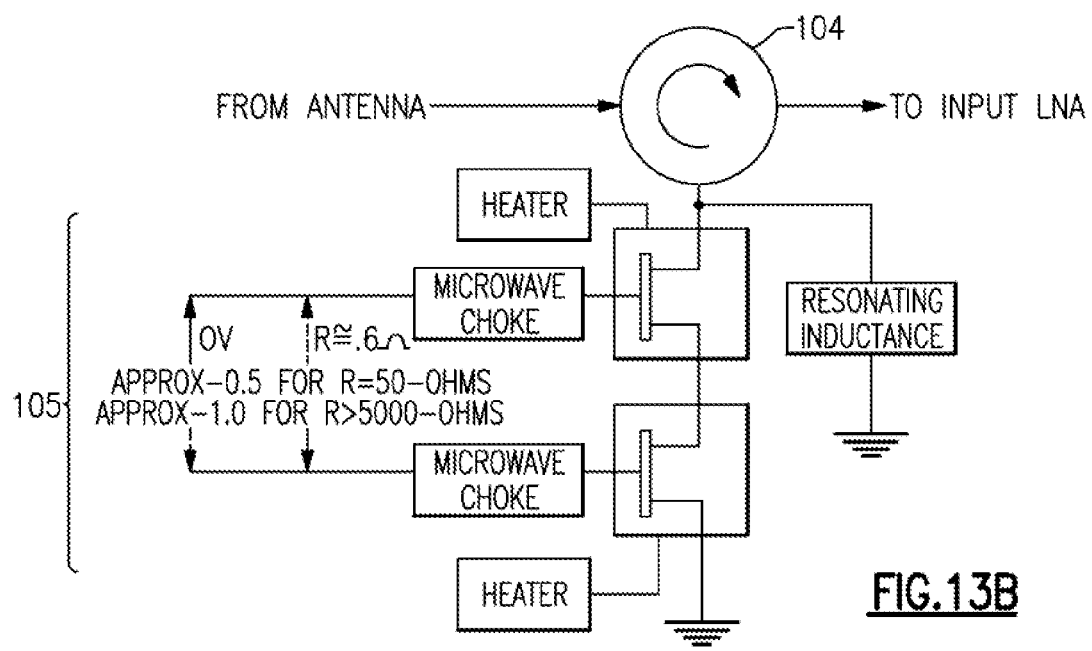
FIG. 13B shows a block diagram of another embodiment of a series arrangement of conductive FETs used as a microwave noise source.

Two possible arrangements are shown in the schematic diagrams of FIG. 13A and FIG. 13B. FIG. 13A shows a block diagram of one embodiment of a parallel arrangement of conductive FETs used as a microwave noise source. Note that one advantage of the embodiment of FIG. 13A is that the termination can be set to 50 ohms with a single device (i.e. the non-selected parallel device essentially presents an open circuit). FIG. 13B shows a block diagram of another embodiment of a series arrangement of conductive FETs used as a microwave noise source. The circuit of FIG. 13B can be simpler to implement on a microstrip circuit because of the in-line arrangement. By contrast, note that in the arrangement of FIG. 13A, the two drain connections should preferably be situated very close to each other to avoid the detuning effect of open circuit stubs. However, the series arrangement of FIG. 13B leads to the total noise as calculated from knowledge of the resistance and temperature of each device where one of the two devices dominates as the contributing noise source (e.g. a first device set to 45 ohms), but the other device (e.g., 5 ohms) still has some effect on the combined (e.g., 50 ohm) noise source. Note that the microwave chokes in both of the embodiments of FIG. 13A and FIG. 13B are used to isolate the DC bias voltage (described above) from the microwave noise output of the heated microwave noise source as applied to an input of the circulator 104.

Figure 13C:
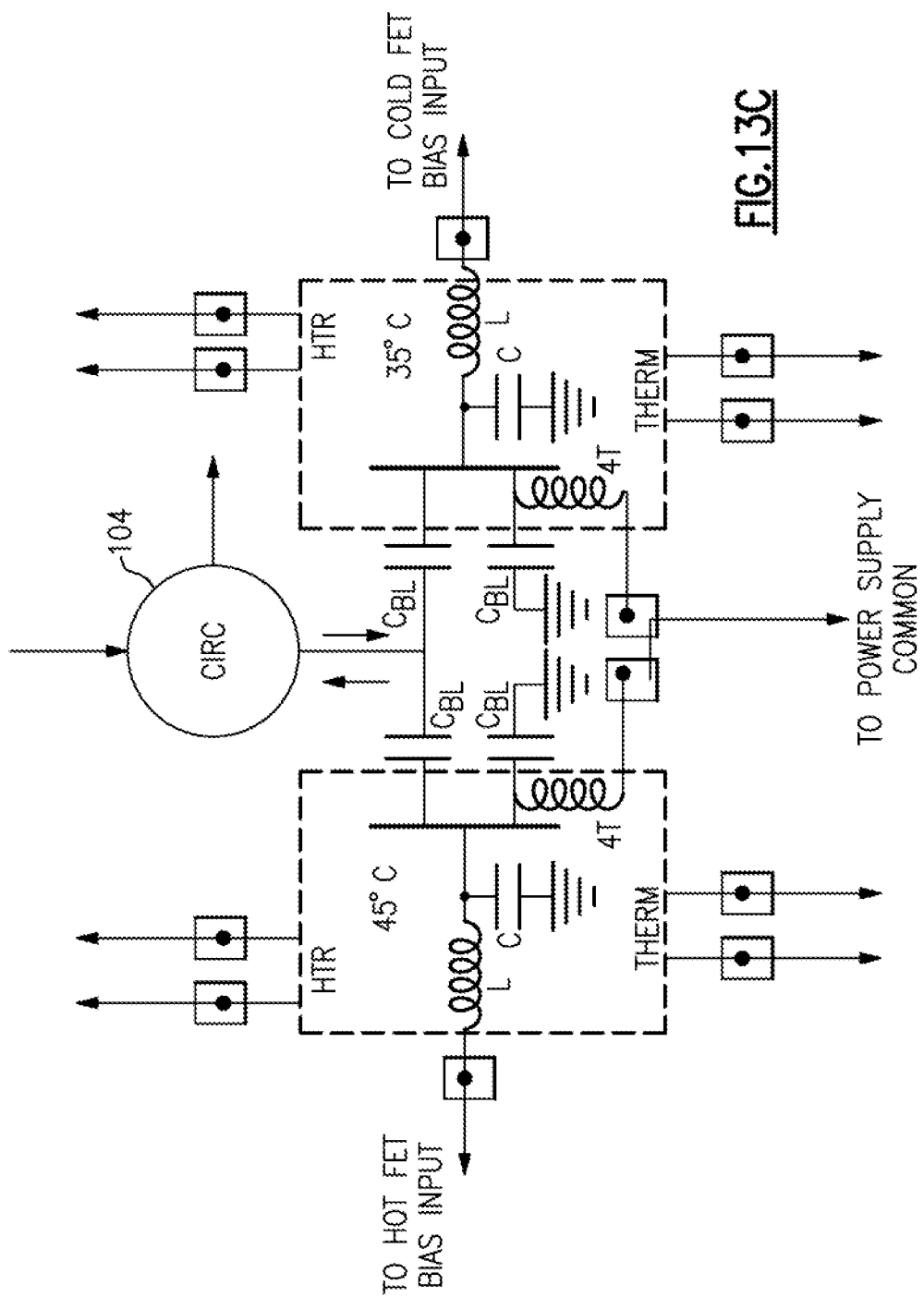
FIG. 13C shows a schematic diagram of one exemplary embodiment of a noise source according to the block diagram of FIG. 13A.

FIG. 13C shows a schematic diagram of one exemplary embodiment of a noise source according to the block diagram of FIG. 13A. Blocking capacitors CBL apply a noise signal from either the 45° C. noise source or the 35° C. noise source to circulator 104. The 45° C. or 35° C. noise source is selected by applying about −0.5V to the respective gate circuit of the desired FET to set its resistance to 50 ohms. The non-selected noise source is set to an open circuit (R>5,000 ohms) by applying −1.0 V to that FET putting it into a "pinch-off" mode. L and C components serve to isolate the DC bias control signals from the RF microwave path to circulator 104.

We turn now to the topic of describing various measurements in terms of depth of measurement into a patient's body, generally related to microwave depth of penetration. In the general cases described above, such using an X-slot antenna 101, the resultant temperature measurement is to a depth related to the beamwidth of the radiometer. For example, it would be useful to eliminate the effects of surface skin temperatures on radiometer readings. A medical microwave radiometer operating over a single frequency band measures the fraction of thermally generated microwave noise that is emitted by subsurface tissues and the skin that reaches and is received by its antenna. The radiometer converts the measured amount of received microwave noise over this single frequency band to an "average" tissue temperature that is a function of both skin temperatures and temperature depth profiles of the subsurface tissues. Interpreting these average tissue temperatures can be difficult. For example, one problem is that subsurface tissue temperatures in general differ from the skin surface temperature wherein the temperature varies with distance from the skin. Microwave emissions from deep-seated subsurface tissues must first pass through the overlying subsurface tissues and through the skin before reaching the radiometer antenna. The overlying tissues and the skin attenuate the thermal microwave emissions from the more deep-seated subsurface tissues and contribute thermal microwave emissions of their own. Such effects were described by one of the co-inventors, F. Sterzer, in "Microwave Radiometers for Non-invasive Measurements of Subsurface Tissue Temperatures", Automedica, pgs. 203-211, vol. 8, 1987.

The temperature versus depth profiles of tissues can be estimated with single frequency radiometers by measuring the thermally generated noise from the tissues using antennas with different depth of penetration into the tissues. These tissue temperature profiles can then be estimated from the known microwave properties of the tissues and the known antenna patterns produced by the different antennas into these tissues by using the equation of radiation transfer. For example, consider the case where one wants to cancel out the effect of skin temperature from a tissue temperature measurement. Two antennas can be used: one antenna has a shallow depth of penetration that includes mostly skin, while the remaining antenna has a depth of penetration that reaches deep into subsurface tissues. Let us assume that the subsurface tissues are all at temperature T1 and the skin is at temperature T2 and has a thickness t and attenuation constant α. When the antenna with the shallower depth of penetration is used, the radiometer will read T2. When the antenna with deep depth of penetration is used the radiometer will read T' which − from the equation of radiation transfer is given by:

$$T' \approx T' \exp{-\alpha t} + T_2(1 - \exp{-\alpha t}) \quad (1)$$

Equation 1 is based on a one dimensional analysis and assumes that there are no reflections at the interface of the subsurface tissues and the skin, and that the subsurface tissues are thick. Rewriting equation (1) yields the following expression for the subsurface tissue temperature $$T_1 \beta T' \exp{+\alpha t} - T_2(1 - \exp{+\alpha t} - 1) \quad (2)$$

T2 and T' are measured quantities. The attenuation constant of the skin a can be estimated from available tables of attenuation constants for tissues with high water content as functions of frequencies (such as described by Johnson and Guy in "Nonionizing Electromagnetic Wave Effects in Biological Materials and Systems", Proceedings of the IEEE, vol. 60, pp 692-718, June 1972) and the thickness of the skin from an examination of the skin over which the antennas are placed.

Eliminating the effects of skin temperatures on radiometer readings can be done automatically by either mechanically or electronically changing the depths of penetration of the radiometer. In some embodiments, the depths of penetration of the radiometer antenna can be varied from short to deep penetration, followed by cancellation of the effects of the skin temperatures from the readings from the deep penetration antenna. Such cancellation can be done by an algorithm running, for example, on a computer 105. In other embodiments, several antenna settings, each with different depths of penetration, can approximate tissue temperatures versus distance into the body. Profiles can then be calculated from the equation of radiation transfer. For example, the depth of penetration of microwave antennas is inversely proportional to their apertures. The apertures can be easily changed by mechanical means. Suitable such antennas have been described by Turner and Kumar in "Computer Solutions for Applicator Heating Patterns", NCI Third International Symposium: Cancer Therapy, Hyperthermia, Drugs, and Radiation, monograph 61, pgs. 521-523, June 1980. Very deep penetrations could be achieved by using antennas with concentrating lenses such as have been described by Nikawa et al. in "Development and Testing of a 2450-MHz Lens Applicator for Localized Microwave Hyperthermia", IEEE Trans. MTT November 1985. Alternatively and in lieu of a shallow antenna, as described herein, an IR sensor can also be used to read the skin temperature directly.

Figure 14A:
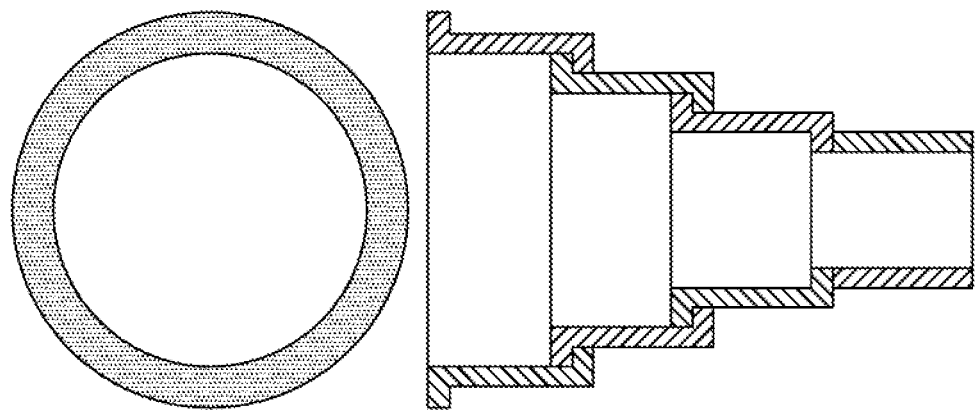
FIG. 14A shows a cutaway view of a collapsing waveguide antenna (in an extended position) having a large aperture and a narrow bandwidth.
Figure 14B:
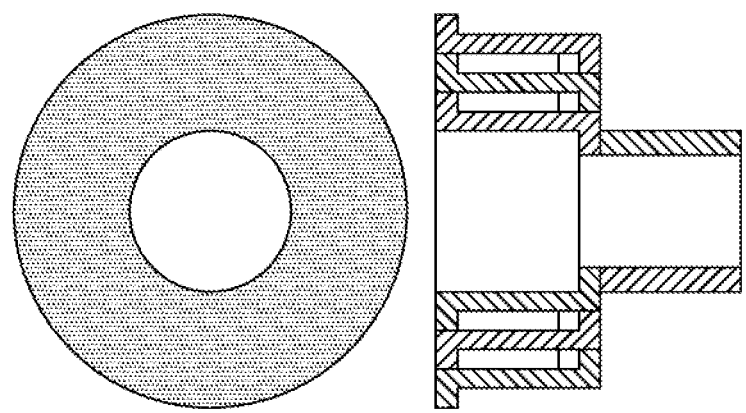
FIG. 14B shows a cutaway view of the collapsing waveguide antenna of FIG. 14A in a collapsed position having a small aperture and a wide bandwidth.

FIG. 14A and FIG. 14B show a cutaway view of a collapsing waveguide means for varying beamwidth and thus depth of penetration. FIG. 14A shows a cutaway view of a collapsing waveguide antenna (in an extended position) having a large aperture and a narrow beamwidth. FIG. 14B shows a cutaway view of the collapsing waveguide antenna of FIG. 14A in a collapsed position having a small aperture and a wide beamwidth.

Now, we turn to a means for electronically varying the locations from which the thermally generated noise from tissues is received. As described above, there can be antennas with different depths of penetration for non-invasively measuring tissue temperature depth profiles with a microwave radiometer operating over a single frequency band. For example, a collapsible waveguide radiometer antenna for mechanically varying the depths from which most of the thermally generated noise by tissues is received was described. A means for electronically that can vary both the depths and also the locations from which most of the thermally generated noise is received is now described.

Figure 15:
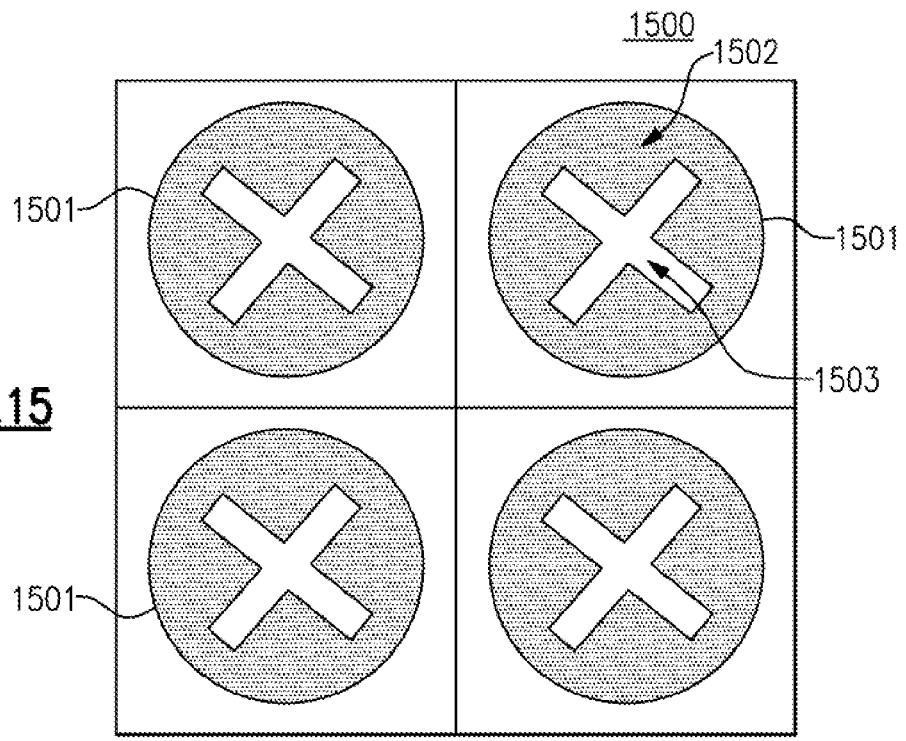
FIG. 15 shows one exemplary array of four microstrip X-slot antennas.
Figure 16:
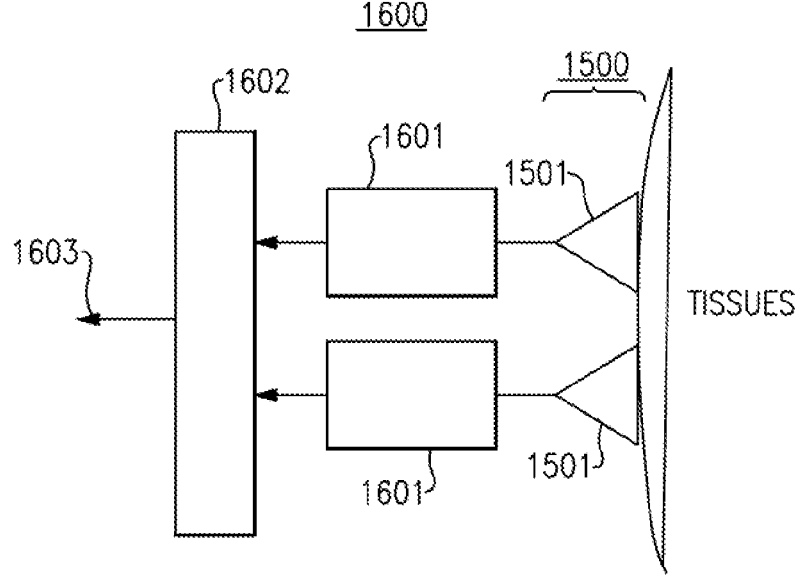
FIG. 16 shows a block diagram of one exemplary embodiment of a steerable microwave radiometer phased array antenna system.

FIG. 15 shows one exemplary array of four microstrip antennas each having two orthogonal intersecting slots (e.g., X-slot antennas 1501). Such antennas can, for example, be produced by etching an X-slot opening 1503 into a metalized layer 1502 on the topside of a microstrip substrate. FIG. 16 shows a block diagram according to one exemplary embodiment of a steerable microwave radiometer phased array antenna system 1600 using the antenna array 1500 of FIG. 15. The steerable microwave radiometer of FIG. 16 can electronically steer the antenna array 1500 for varying the depths and locations from which most of the thermally generated noise from tissues are received. The phases of the thermally generated microwave noise received from the tissues by each antenna can be varied electronically by means of microwave phase shifters 1601, such as, for example, by varactor diode phase shifters, a type of microwave phase shifter well known in the art. After the phase of the microwave noise is electronically set in each arm of the four antennas, the outputs of the four arms are combined, such as by use of combining circuit 1602, and fed via an output 1603 combining circuit 1602 to a microwave radiometer amplifier (not shown). Such phased arrays have been described for other uses, such as for RADAR applications, by Brown, in "Directional Antennas", Proc. IRE, Vol. 25, No. 1, January, 1937, and Skolnik, in the Radar Handbook. Second Edition, Chapter 7.2 "Array Theory", McGraw Hill Publishing Company, 1990. The relative settings of the phase shifters 1601 in the arms of the four antennas 1501 determine the amount of thermal noise power that reaches the radiometer from the various parts of the tissues because the electric fields received at each antenna are linearly added in the combiner 1602 that feeds the radiometer amplifier (not shown). For example, if the phases are adjusted so that the thermal noise powers generated at a given point in the tissues arrive in phase at each antenna 1501, the contribution to the thermal noise power received by the radiometer from this point in the tissues will be maximized. Similarly, neglecting any differences in losses in the tissues to each of the four antennas encountered by the thermal noise generated at a given point in the tissues, if the relative phases are adjusted so that the thermal noise powers generated at a given point in the tissues arrive in phase at two of the antennas but out of phase at the two other antennas, the contribution to the thermal noise power received by the radiometer from this point in the tissues will be minimized. Thus by electronically varying the settings of the relative phase shifts between the four antennas and measuring the noise power at each setting by means of the radiometer, it becomes possible to estimate the temperature distributions in the neighborhood of the antennas. To improve an estimate of the microwave properties over the frequency band of the radiometer of the tissues whose temperature profile is being measured, calculations based on signals received from various parts of the body can include corrections for the relevant microwave properties of muscle, skin, and other tissues with high water content, as well as those of fat, bone, and other tissues with low water content.

Figure 17:
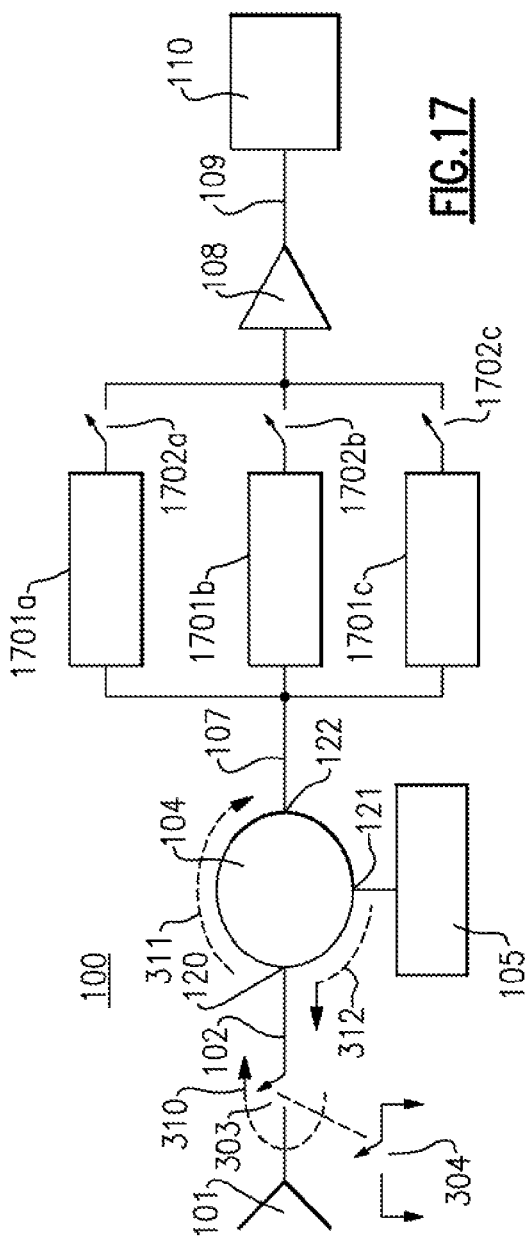
FIG. 17 shows a block diagram of an embodiment of a microwave radiometer that can operate over a multiple frequency bands

FIG. 17 shows another embodiment of a microwave radiometer 100 that can non-invasively measure tissue temperature at different depth ranges using a microwave radiometer that can operate over multiple frequency bands. The circuit function blocks from antenna 101 through circulator 104 have a bandwidth BW wide enough to accommodate "N" sections of tuned filters, each of the N sections having a bandwidth that is a subset (narrower) than BW of the front end sections. Each bandwidth provides tissue temperatures from different depths of penetration. In the exemplary embodiment of FIG. 17, N=3 and switches 1702a to 1702c can be closed one at a time to select one of three available bandwidths from filters 1701a to 1701c. There can be additional switch contacts (not show) to provide an indication to computer 150 which bandwidth has been selected. Also, switches 1701a to 1701c can be mechanical microwave switches, such as microwave relays, or electronic switches, such as electronic switches. Either electro-mechanical switches or electronic switches can be controlled by an algorithm running on computer 150. Note that while the embodiment of FIG. 17 was based on the microwave radiometer of FIG. 4 having a normally-open switch 303, a multiple frequency band radiometer 100 can also use a normally closed switch such as in the embodiment of FIG. 2.

Now turning to the algorithm that typically runs on computer 150, FIG. 2, calculations are discussed in more detail along with numerical examples. Before discussing the calibrate-measure cycles in more detail, note that in addition to RF gain and offset (calibrate mode) and emissivity and body core temperature (measure mode), there can be other measured correction factors. For example, the temperature of the microwave circulator (e.g. 104, FIG. 2) as well as the skin surface temperature (as discussed above) can also be measured and used for correction purposes.

Figure 18:
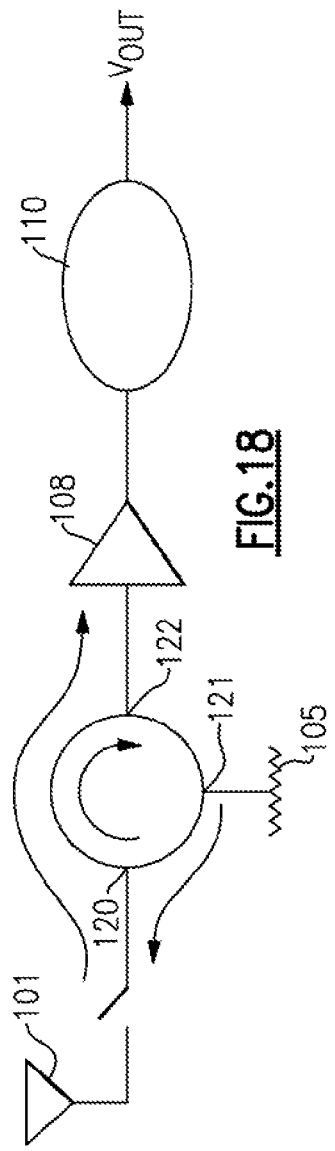
FIG. 18 shows a simplified block diagram of a microwave radiometer for illustrating a circulator temperature correction.

FIG. 18 shows a simplified block diagram of a microwave radiometer, such as a handheld radiometer 100 for purposes of illustrating a circulator temperature correction. Circulator 104 routes the thermal noise from heater termination 105 to the open switch 303, FIG. 4 (calibrated mode), whence it is reflected into the measurement path (LNA 108, detector 110, FIG. 4). When switch 303 (see also FIG. 4) is closed the measure path (measure mode) is the same as the path in the calibrate mode, except for the section from circulator port 121 to circulator port 120. By prior measurement of the section from circulator port 121 to circulator port 120, $\alpha_{CIRC}$, expressed as a loss in ratio form, and a current measurement of the circulator temperature ($T_{CIRC}$), the termination measured temperatures can be further corrected as follows:

$$T_{refcorrected} = [T_{refmeas}(1-\alpha_{CIRC})] + [T_{CIRC}(\alpha_{CIRC})]$$

EXAMPLE

Circulator Correction $\alpha_{CIRC}$ is measured as −0.5 dB or 0.11; $T_{CIRC}$=30.0° C., and $T_{ref(measured)}$=45° C.

Thus in the "hot condition" heated termination 105 has a corrected reference temperature calculated as follows:

$$T_{refcorrected} = 45° C.(0.89) + 30.0° C.(0.11) = 40.05° C. -3.3° C. = 43.35° C.$$

and in the "cold condition" heated termination 105 has a corrected reference temperature calculated as follows:

$$T_{refcorrected} = 35° C.(0.89) + 30.0° C.(0.11) = 31.15° C. -3.3° C. = 34.45° C.$$

Skin temperature can likewise be used for a correction to the final reading using a similar formula. After the radiometer temperature is calculated ($T_{RAD}$), the skin temperature is measured ($T_{SKIN}$). The attenuation of the skin layer had been approximated from data in the literature data about skin thickness and skin tissue attenuation permitting generation of skin attenuation ($\alpha_{SKIN}$). The corrected core temperature can then be(calculated as follows:

$$T_{RAD} = [T_{CORE}(1-\alpha_{SKIN})] + [T_{SKIN}(\alpha_{SKIN})]$$

EXAMPLE

Skin Temperature Correction $T_{RAD} = T_{CORE}(1-\alpha_{SKIN}) + T_{SKIN}(\alpha_{SKIN})$, assuming $T_{SKIN}$(measured)=30.0° C.; $T_{RAD}$=36° C. and $\alpha_{SKIN}$=0.5 dB or 0.11.

$T_{CORE}=(36°\text{ C}.-3.3°\text{ C})/0.89=36.74°\text{ C}.$

Now describing the calibrate and measure calculation in more detail, assuming the circulator corrections have been made, consider the following four measured parameters of the reference temperature and detector output voltage, in the calibrate mode: $T_{CC}$ (temperature calibrate-termination cold), $V_{CC}$ (detector voltage calibrate-cold), $T_{CH}$ (temperature calibrate-termination hot), $V_{CH}$ (detector voltage calibrate-hot); and in the measure mode: $T_{MC}$, (temperature measure-termination cold), $V_{MC}$, $T_{MH}$ (temperature measure-termination hot), $V_{MH}$ (detector voltage measure-hot).

EXAMPLE

Calibrated/Measure Cycle

In the calibrated mode: $T_{CC}$=35° C., $V_{CC}$=100 µV, $T_{CH}$=45° C., $V_{CH}$=105 µV. From the equation of line (slope and offset):

$$T = \frac{V+A}{B},$$

where T is heated termination temperature, V is detector voltage, and A and B are constants, which reduces to:

$$B = \frac{\Delta V}{\Delta T}$$

and, $A=BT_L-V_L$ or, $BT_H-V_H$. Therefore:

$$B = \frac{5 \text{ µV}}{10° \text{ C.}} = 0.5 \text{ µV}/°\text{ C.};$$
$$A = (0.5)35 - 100 = -82.5 \text{ µV, or}$$
$$A = (0.5)45 - 105 = -82.5 \text{ µV, and}$$
$$\text{Temp} = \frac{(V-82.5) \text{ µV}}{0.5 \frac{\text{µV}}{°\text{ C.}}}$$

Then, for example, for a measured detector output voltage of 102.5 µV, the core temperature is calculated as 40° C. Thus, in the measure mode, $V_{MC}$=102 µV for $T_{MC}$=35° C., and $V_{MC}$=103 µV for $T_{MC}$=45° C.

Notice that if the match between the antenna and tissue were perfect (ρ=0), there would be no difference in the readings at the two reference temperatures, i.e., all of the noise power from the heated references would be absorbed in the tissues. Because of reciprocity, that means that all of the thermal noise from the tissue is received by the antenna (e.g. no mismatch). Conversely, if the two detector voltages are the same as during the calibration mode, none of the thermal noise is received by the antenna (e.g. a perfect mismatch (ρ=1). It can be shown that ρ is the ratio of the temperatures calculated from the detector voltages by:

$$\rho = \frac{\Delta T(\text{measurement})}{\Delta T(\text{calibrate})}$$

EXAMPLE

Calibrated/Measure Cycle

Measure Mode:

$$T_{LOW} = \frac{V_{LOW} - 82.5}{0.5}; T_{HIGH} = \frac{V_{HIGH} - 82.5}{0.5}$$
$$T_{LOW} = \frac{102 - 82.5}{0.5} = 39.0° \text{ C.}; T_{HIGH} = \frac{103 - 82.5}{0.5} = 41.0° \text{ C.}$$

In a delta T measurement mode: 41° C.−39° C.=2° C.
Measure Mode: $T_{LOW}$=35° C./$T_{HIGH}$=45° C., delta T=10° C., $$\rho = \frac{2}{10} = 0.2.$$

To compute the radiometer temperature ($T_{RAD}$) with ρ correction and measured antenna temperature ($T_A$, the true thermal noise from tissues) for each condition:

$$T_{RAD} = T_A(1-\rho) + T_{TERM}(\rho) \text{ or, } T_A = \frac{T_{RAD} - T_{TERM}(\rho)}{1-\rho}$$

For the cold condition:

$$T_A = \frac{39°\text{ C.}-0.2(35°\text{ C.})}{0.8} = 40° \text{ C.,}$$

and for the hot condition:

$$T_A = \frac{41°\text{ C.}-0.2(45°\text{ C.})}{0.8} = 40° \text{ C.}$$

Note that if all of the measurements and calculations are correct, the cold condition $T_A$ should equal the hot condition $T_A$.

Returning to a description of a hand held radiometer as part of a system including an external computer 150 (FIG. 2), a hand held radiometer can be tethered or wirelessly linked to a computer or assembly including a computer. In passing it should be noted that the construction need not be limited to an external computer linkage, wherein, for example, the handheld radiometer housing can be configured to enclose all of the components, including an internal microprocessor, ADC and LNA, wherein each of the preceding can be interconnected, for example, by a suitable printed circuit board design. A connecting cable can be used to tether the handheld housing in one version, the cable being a convention copper based cable with wires and/or shielded wires. The cable can have one or more electrical connectors, or in some embodiments, a tether cable can be non-removable. We define an electrical connection means herein to include any wired cable or tether (a wired electrical or electro-optical connection, such as fiber optics) to a hand held microwave radiometer (e.g. radiometer 100, FIG. 2), including both releasable embodiments (e.g. including a traditional shelled connector) and non-releasable hardwired connections. Note that since the microwave antenna (e.g. antenna 101, FIG. 2) is colocated in a handheld microwave radiometer housing, any external connection (i.e. via an electrical connector) to radiometer 100 generally does not need a microwave cable.

Turning now to control signals, switching or toggling between temperatures of a heated termination (e.g. heated termination 105, FIG. 2) can be accomplished by timing signals sent via the electrical connector, such as from an external computer 150. Or, there can be another external control box (not shown) that generates timing for toggling the heated termination. Timing can be generated by firmware running on a computer, or by any other suitable digital or analog timing generator. Or, in other embodiments, a timing circuit that causes the toggling of the heated termination can be included in the radiometer housing (not shown). Regardless of how the timing signals that toggle the heated termination are generated, as described above, the ADC that digitizes the detector output signal (e.g. the output of detector 110, FIG. 2) should digitize when the temperature of the heated termination has reasonably stabilized (e.g. at T1 or T2). Note that a timing coordination between, for example, the ADC and heated termination is completely unrelated to the complexity of a Dicke switch and corresponding synchronous demodulator, that is no longer needed in the new handheld radiometer.

Similarly, the ADC (e.g. ADC 151, FIG. 2) can be located inside of a computer 150, such as on an ADC card that plugs into a computer 150, in a separate box, or included in the hand held radiometer housing (not shown). Alternatively, the ADC can be included within a computer, such as within a microcomputer. As discussed above, the ADC digitization times are substantially timed to take data (e.g. to digitize the detector output signal) when the temperature of the heated termination is reasonably stable at a desired temperature.

We turn now to a computer (e.g. computer 150, FIG. 2) for running an algorithm to execute the calibration and measure modes of a handheld radiometer. In some embodiments, as described above, hand held radiometer 100 is tethered by at least one electrical connector to an external computer 150. However, in other embodiments (not shown), the handheld radiometer can include a computer located within the hand held radiometer housing. In such cases, the calibration and measure mode computation can be accomplished onboard wherein the hand held radiometer and digital data, such as digital data representing the temperature measurement, can be transmitted via the electrical connector from the handheld radiometer or alternatively by means of the display of the housing.

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the preferred mode as illustrated in the drawing, it will be understood by one skilled in the art that various changes in detail may be affected therein without departing from the spirit and scope of the invention as defined by the claims.

We claim:

1. A microwave handheld radiometer for measuring subsurface tissue temperature of a subject, said radiometer comprising:
  a microwave antenna disposed relative to a handheld radiometer housing and adapted to electromagnetically couple to a skin surface of a subject;
  a circulator having a first circulator input and a second circulator input, said first circulator input electrically coupled to said antenna via a microwave feedline;
  a switch electrically disposed between said antenna and said microwave feedline, said switch having a calibrate state and a measure state;
  a noise source electrically coupled to said circulator, said noise source being configured to provide a first source of thermal noise at a first temperature and a second source of thermal noise at a second temperature and wherein said noise source is switched between said first source and second source upon external command; and
  a detector creating a detector output wherein said radiometer further including means for toggling said switch between said states, in which said switch is placed into said measure state automatically based on a threshold reading of a proximity sensor disposed on said housing, said proximity sensor providing a signal indicative of distance from said subject and including at least one sensor for measuring surface temperature of said subject.

2. The handheld radiometer of claim 1, wherein said detector output is electrically coupled to an analog to digital converter (ADC).

3. The handheld radiometer of claim 1, wherein said toggling means further includes a mechanical component which is configured to be movable into direct physical contact with the skin of a subject, wherein moving said component into direct physical contact also automatically toggles said switch into said measure state.

4. The handheld radiometer of claim 3, wherein said switch comprises a first normally-open switch electrically disposed between said antenna and said first circulator input.

5. The handheld radiometer of claim 4, wherein said first normally-open switch comprises a first spring loaded contact.

6. The handheld radiometer of claim 5, further comprising a second spring loaded contact configured to provide a second normally-open switch to provide an indication of whether said switch is in a selected one of said calibrate state and said measure state.

7. The handheld radiometer of claim 6, wherein said handheld radiometer is communicatively coupled to a computer, said computer being configured to run an algorithm that computes a first set of calibration coefficients when said switch is sensed to be in said calibrate state, and using said first set of coefficients said algorithm computes an antenna emissivity coefficient and a temperature when said switch is sensed to be in said measure state.

8. The handheld radiometer of claim 6, further comprising a computer configured to run an algorithm that computes a first set of calibration coefficients when said switch is sensed to be in said calibrate state, and using said first set of coefficients, said algorithm computes an antenna emissivity coefficient and a temperature when said switch is sensed to be in said measure state and said temperature is communicatively coupled as a digital temperature output.

9. The handheld radiometer of claim 1, wherein said surface measuring sensor is one of a thermistor and an IR temperature sensor.

10. The handheld radiometer of claim 9, including at least one heater element for heating said IR sensor or thermistor to a predetermined temperature.

11. The handheld radiometer of claim 10, wherein at least one proximity sensor is connected to a computer, said IR sensor and said at least one heater element such that a first threshold signal indicative of a first distance between said surface and said IR sensor engages said at least one heater element and a second threshold signal indicative of a second distance between the skin surface and said IR sensor automatically causes activation of said IR sensor.

12. The handheld radiometer of claim 1, wherein said switch comprises a normally-closed switch electrically disposed between said antenna and an electrical ground.

13. The handheld radiometer of claim 1, further including an amplifier, said amplifier being electrically powered by a power source electrically connected via at least one electrical connector.

14. The handheld radiometer of claim 13, wherein said amplifier is electrically powered by at least one battery disposed with said handheld radiometer housing.

15. The handheld radiometer of claim 13, wherein said antenna comprises an array of N antennas, and wherein each antenna of said array of N antennas is electrically coupled to a phase shifter and an electrical output of each of said phase shifters is electrically coupled to a combining circuit and an output of said combining circuit is electrically coupled to said amplifier.

16. The handheld radiometer of claim 15, further comprising N filters disposed between said circulator and said amplifier, each of said filters having a microwave bandwidth corresponding to an average tissue depth.

17. The handheld radiometer of claim 1, wherein said noise source comprises a single resistive element configured to be toggled between two temperatures.

18. The handheld radiometer of claim 1, wherein said noise source comprises two resistive elements.

19. The handheld radiometer of claim 18, wherein each of said two resistive elements comprises a field effect transistor (FET).

20. The handheld radiometer of claim 1, wherein said antenna comprises an X-slot antenna.

21. The handheld radiometer of claim , wherein said antenna further comprises a telescoping waveguide.

22. The handheld radiometer of claim 1, further including means for minimizing the effects of surface temperature on a subsurface temperature measurement.

23. The handheld radiometer of claim 1, wherein said radiometer is used to measure core body temperature.

24. The handheld radiometer of claim 1, wherein said switch is an FET microwave switch.

25. A microwave handheld radiometer for measuring subsurface tissue temperature, said radiometer comprising:
a handheld radiometer housing;
a microwave antenna means for receiving a microwave electromagnetic signal mechanically disposed at a distal end of said handheld radiometer housing and adapted to electromagnetically couple to a skin surface of a mammal;
a circulator having a first circulator input and a second circulator input, said first circulator input electrically coupled to said antenna via a microwave feedline;
a switch means for switching between a calibration mode and a measurement mode;
a noise source means for generating microwave noise at more than one noise temperature, said noise source electrically coupled to a second input of said circulator, said noise source configured to provide a first source of thermal noise at a first temperature and a second source of thermal noise at a second temperature and wherein said noise source is switched between said first source and second source upon external. command;
a detector having a detector output; and
means for toggling said switch means between said modes in which said switch means is switched into said measurement mode automatically based on a threshold reading of a proximity sensor disposed on said housing, said proximity sensor providing a signal indicative of distance from said mammal and including at least one sensor for measuring surface temperature of said mammal.

26. A microwave radiometer system for measuring subsurface tissue temperature, said system comprising:
a microwave antenna adapted to electromagnetically couple to a skin surface of a mammal;
a circulator having a first circulator input and a second circulator input, said first circulator input electrically coupled to said antenna via a microwave feedline;
a switch electrically disposed between said antenna and said microwave feedline, said switch selectively movable between a calibrate state and a measure state;
a noise source configured to provide a first source of thermal noise at a first temperature and a second source of thermal noise at a second temperature and wherein said noise source is switched between said first source and second source upon external command;
a detector having a detector output;
a computer communicatively coupled to a sensor disposed within said radiometer configured to indicate a selected one of:
1) said microwave antenna in a measurement mode when said switch is sensed to be in said measure state, and
2) said microwave antenna in a calibration mode when said switch is sensed to be in said calibrate state; and
means for toggling said switch between said measure and calibrate states in which said switch is switched into said measure state automatically based on a threshold reading of a proximity sensor, said proximity sensor providing a signal indicative of distance from a mammal and including at least one sensor for measuring skin surface temperature of said mammal.

27. The system of claim 26, wherein said computer runs an algorithm wherein said algorithm computes a set of calibration constants in said calibration mode and said algorithm computes and outputs a core body temperature using said set of calibration constants in said measurement mode.

28. A method for determining a core body temperature measurement using a handheld microwave radiometer, said method comprising the steps of:
providing a handheld microwave radiometer including a microwave antenna, a switch including a sensed switch position output and a toggling thermal termination coupled to said handheld microwave radiometer;
calibrating said handheld microwave radiometer to determine a first set of calibration coefficients based on a detector output at a corresponding thermal termination temperature;
measuring a temperature to a depth within a mammalian skin surface as a sub-surface measurement based on an antenna emissivity coefficient calculated from said first set of calibration coefficients and a detector output at each said thermal termination temperature and in which said switch is toggled between measurement and calibration states and in which said switch is caused to open and close based on a threshold reading of a threshold sensor, said threshold sensor providing a signal indicative of distance from a subject and including at least one sensor for measuring skin surface temperature of said subject.

29. A method as recited according to claim 28, wherein said switch is further caused to open and close based on direct physical contact between a portion of said antenna and the skin surface of the subject.

30. A method as recited according to claim 28, wherein said switch is further caused to open and close based on a user-actuable control.

31. A method as recited according to claim 28, wherein said method further comprises the step of correcting sub-surface measurements caused by surface temperature effects.

32. A method as recited according to claim 31, wherein said method further comprises the step of measuring skin surface temperature using said surface temperature measuring sensor wherein said correcting step includes the step of applying a measured skin surface temperature to said sub-surface measurements.

33. A method as recited according to claim 32, wherein said surface measuring sensor is at least one of a thermistor and an IR sensor.

34. A method as recited according to claim 33, further including a step of preheating said IR sensor prior to said skin surface temperature measuring step.

* * * * *